United States Patent
Oh et al.

(10) Patent No.: US 11,932,895 B2
(45) Date of Patent: Mar. 19, 2024

(54) MEDIUM COMPOSITION FOR PRODUCING ALCOHOL FROM SYNTHETIC GAS COMPRISING ETHANOL AND METHOD FOR PRODUCING ALCOHOL USING THE SAME

(71) Applicant: KOREA INSTITUTE OF SCIENCE AND TECHNOLOGY, Seoul (KR)

(72) Inventors: Hyun Ju Oh, Seoul (KR); Youngsoon Um, Seoul (KR); Sun Mi Lee, Seoul (KR); Gyeongtaek Gong, Seoul (KR); Ja Kyong Ko, Seoul (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 0 days.

(21) Appl. No.: 17/849,571

(22) Filed: Jun. 24, 2022

(65) Prior Publication Data
US 2023/0093685 A1 Mar. 23, 2023

(30) Foreign Application Priority Data
Sep. 17, 2021 (KR) .................. 10-2021-0124831

(51) Int. Cl.
C12P 7/06 (2006.01)
C12P 7/16 (2006.01)
C12R 1/145 (2006.01)

(52) U.S. Cl.
CPC .................. *C12P 7/06* (2013.01); *C12P 7/16* (2013.01); *C12R 2001/145* (2021.05)

(58) Field of Classification Search
CPC ........ C12P 7/06; C12P 7/16; C12R 2001/145; Y02E 50/10
See application file for complete search history.

(56) References Cited

U.S. PATENT DOCUMENTS

| | | |
|---|---|---|
| 2007/0275447 A1 | 11/2007 | Lewis |
| 2009/0203098 A1 | 8/2009 | Verser |
| 2016/0215302 A1 | 7/2016 | Haas |

FOREIGN PATENT DOCUMENTS

| | | | | |
|---|---|---|---|---|
| DE | WO 2019/072955 A1 * | 4/2019 | ................ | C12P 7/06 |
| KR | 10-2013-0041923 A | 4/2013 | | |
| KR | 10-2014-0026207 A | 3/2014 | | |
| KR | 10-2016-0092931 A | 8/2016 | | |
| KR | 10-2016-0131239 A | 11/2016 | | |
| KR | 10-1985307 B1 | 6/2019 | | |
| WO | 2012/003376 A2 | 1/2012 | | |
| WO | 2013/176948 A2 | 11/2013 | | |
| WO | 2019/072955 A1 | 4/2019 | | |

OTHER PUBLICATIONS

Oh et al., Production of Hexanol as the Main Product Through Syngas Fermentation by Clostridium carboxidivorans P7. Frontiers n Bioeng. Biotechnol., 2022, vol. 10: 1-11. (Year: 2022).*

Naveira AF., Biofuels production (ethanol, butanol, hexanol) from renewable sources. Doctoral Thesis UDC 2018, Espana, pp. 1-383. (Year: 2018).*

Yasumasa Dekishima et al., "Extending Carbon Chain Length of 1-Butanol Pathway for 1-Hexanol Synthesis from Glucose by Engineered *Escherichia coli*", Journal of the American Chemical Society, 2011, pp. 11399-11401, vol. 133, No. 30.

Clementina Dellomonaco et al., "Engineered reversal of the b-oxidation cycle for the synthesis of fuels and chemicals", Nature, 2011, pp. 355-359, vol. 476.

John R. Philips et al., "Butanol and hexanol production in Clostridium carboxidivorans syngas fermentation: Medium development and culture techniques", Bioresource Technology, 2015, vol. 190, pp. 114-121.

Sara Ramio-Pujol et al., "Incubation at 25° C. prevents acid crash and enhances alcohol production in Clostridium carboxidivorans P7", Bioresource Technology, 2015, pp. 296-303, vol. 192.

Yi-Fan Han et al., "Combination of Trace Metal to Improve Solventogenesis of Clostridium carboxidivorans P7 in Syngas Fermentation", Frontiers in Microbiology, 2020, pp. 1-12, vol. 11.

Shaohuang Shen et al., "Effect of temperature and surfactant on biomass growth and higher-alcohol production during syngas fermentation by Clostridium carboxidivorans P7", Bioresources and Bioprocessing, 2020, pp. 1-13, vol. 7, No. 56.

Shota Atsumi et al., "Non-fermentative pathways for synthesis of branched-chain higher alcohols as biofuels", Nature, 2008, pp. 86-89, vol. 451.

Yunsu Lee et al., "Ketonization of hexanoic acid to diesel-blendable 6-undecanone onthe stable zirconia aerogel catalyst", Applied Catalysis A: General, 2015, pp. 288-293, vol. 506.

Ánxela Fernández Naveira et al., "Production of chemicals from C1 gases (Co, CO2) by Clostridium carboxidivorans", World J Microbiol Biotechnol, 2017, pp. 1-11, vol. 33, No. 43.

Hyun Ju Oh et al., "Effect of Culture Conditions on Hexanol Production from Syngas by Clostridium carboxidivorans P7," 2021 KSBB Spring Meeting and International Symposium, Apr. 14-16, 2021.

Request for the Submission of an Opinion for Korean Patent Application No. 10-2021-0124831, dated Dec. 15, 2023.

* cited by examiner

*Primary Examiner* — Ganapathirama Raghu

(57) ABSTRACT

The present disclosure relates to a composition for preparing hexanol or butanol and a method for preparing hexanol or butanol using ethanol and synthesis gas, wherein the composition according to an aspect of the present disclosure is a medium composition containing ethanol as an active ingredient, and by culturing a strain producing hexanol or butanol after inoculating with a medium containing the composition and supplying synthesis gas, hexanol or butanol can be prepared economically using inexpensive synthesis gas, and hexanol or butanol can be prepared with high efficiency by focusing the flow of a carbon source consumed in a fermentation process to the production of hexanol or butanol.

7 Claims, 19 Drawing Sheets

[FIG. 1A]
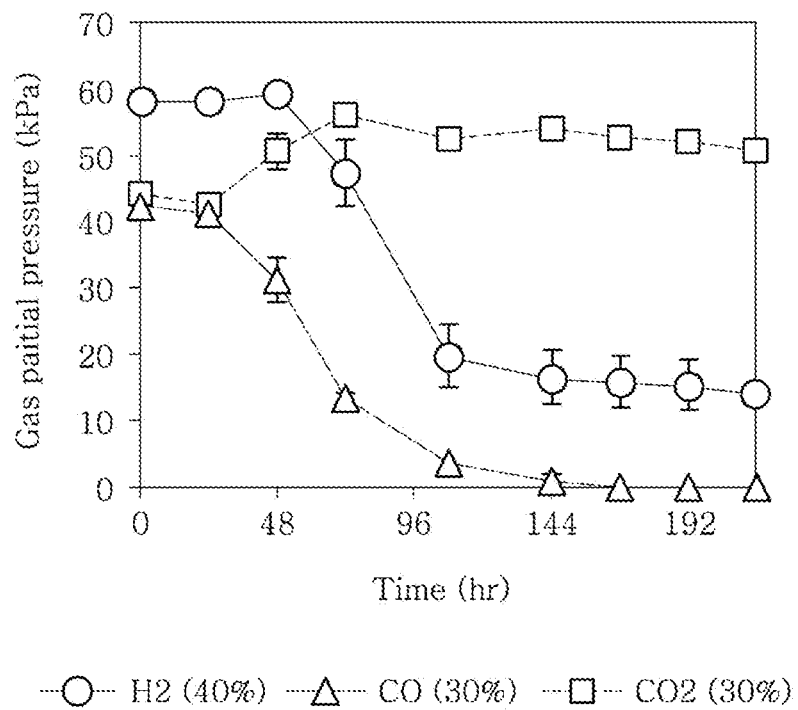

[FIG. 1B]
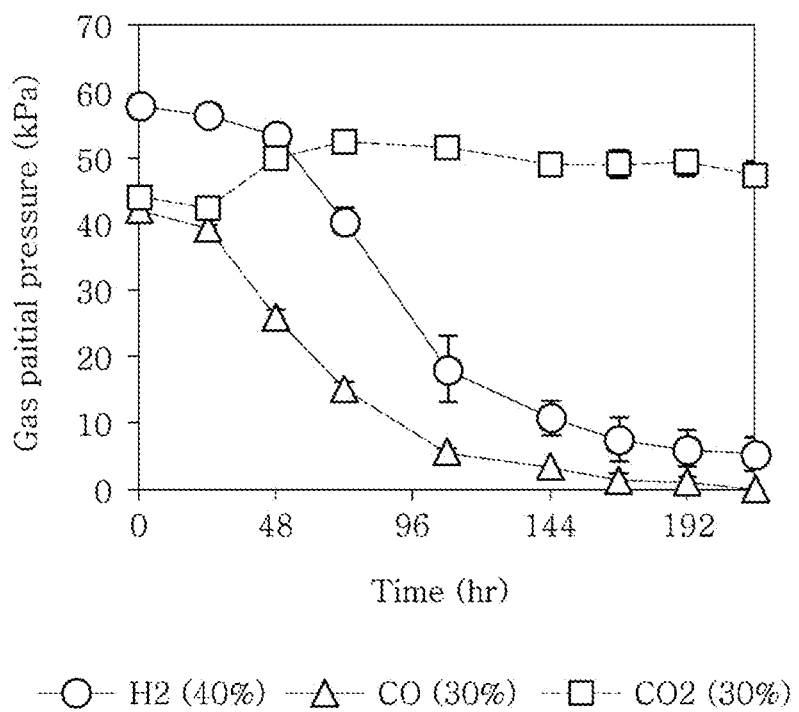

[FIG. 1C]
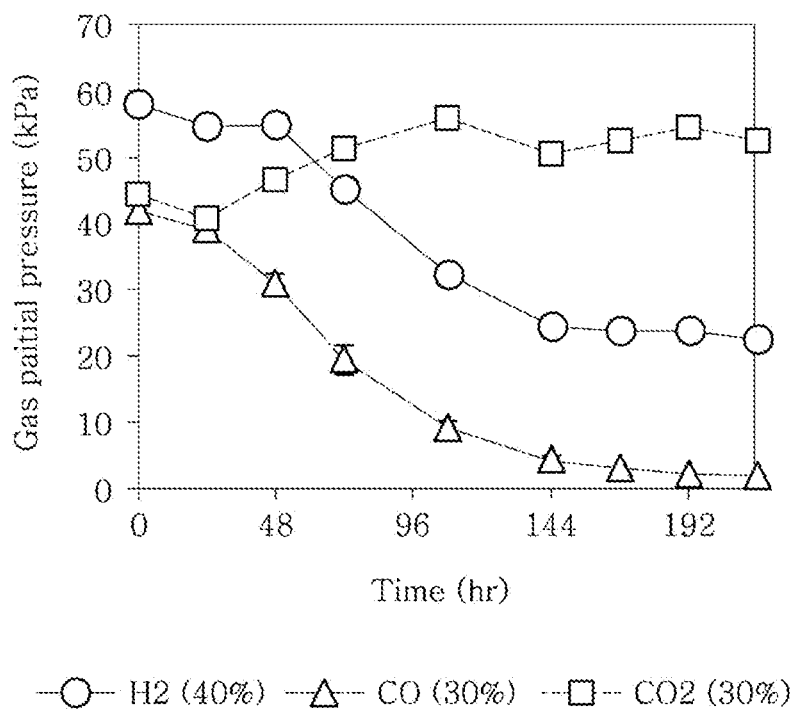

[FIG. 1D]
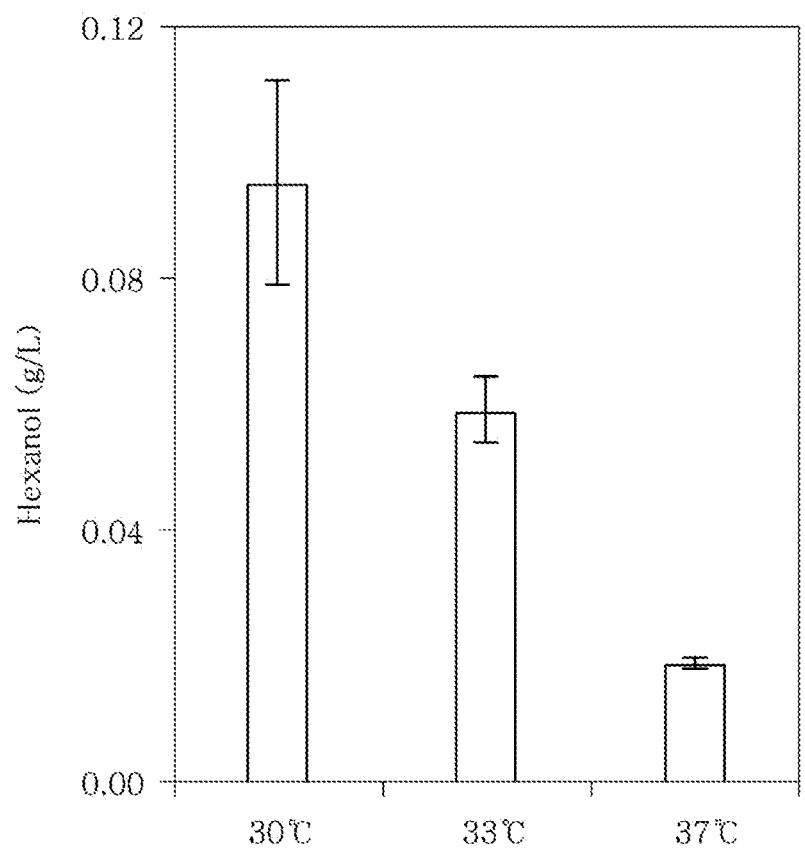

[FIG. 1E]
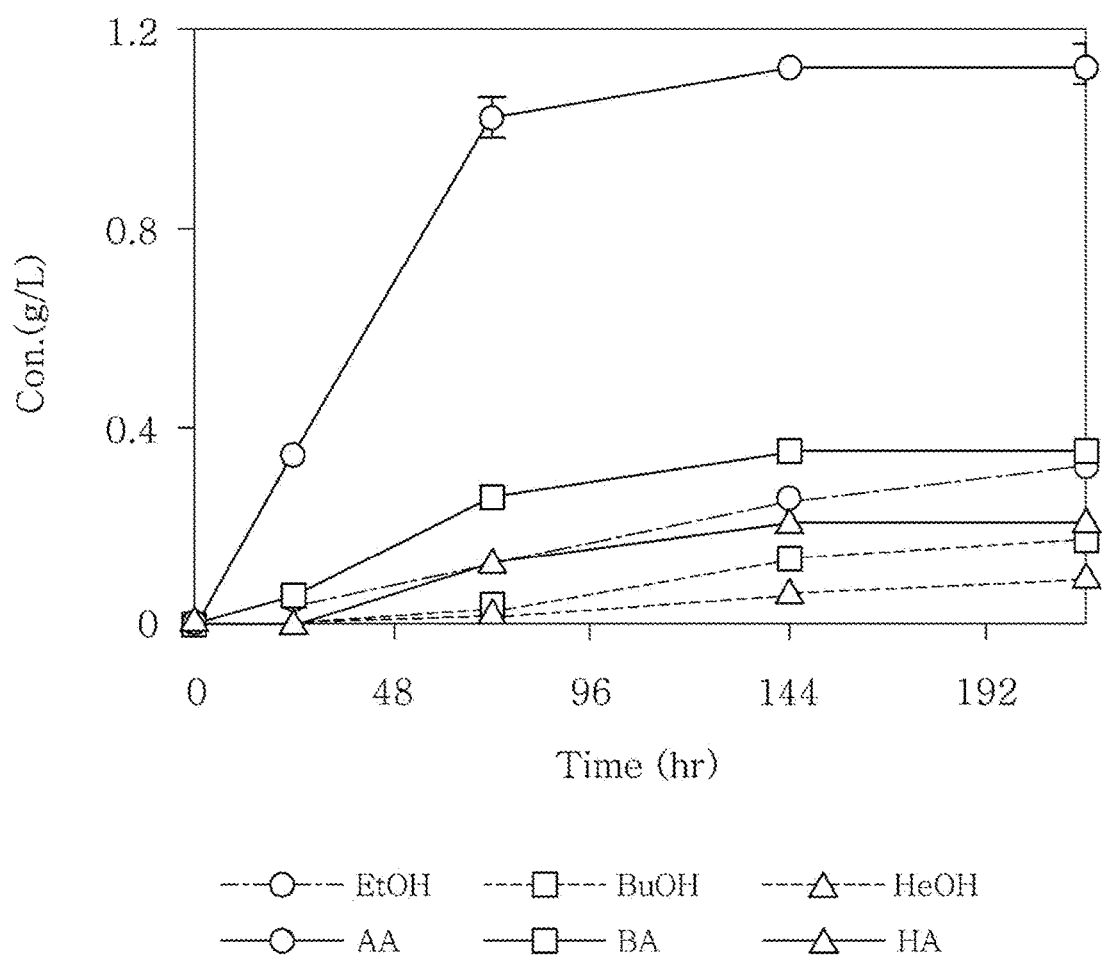

[FIG. 2A]
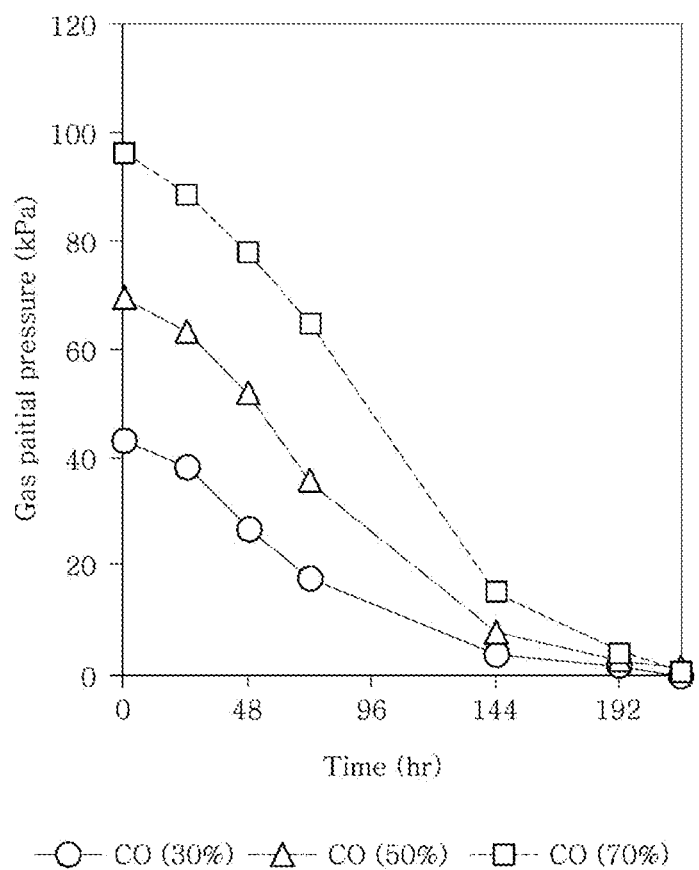

[FIG. 2B]
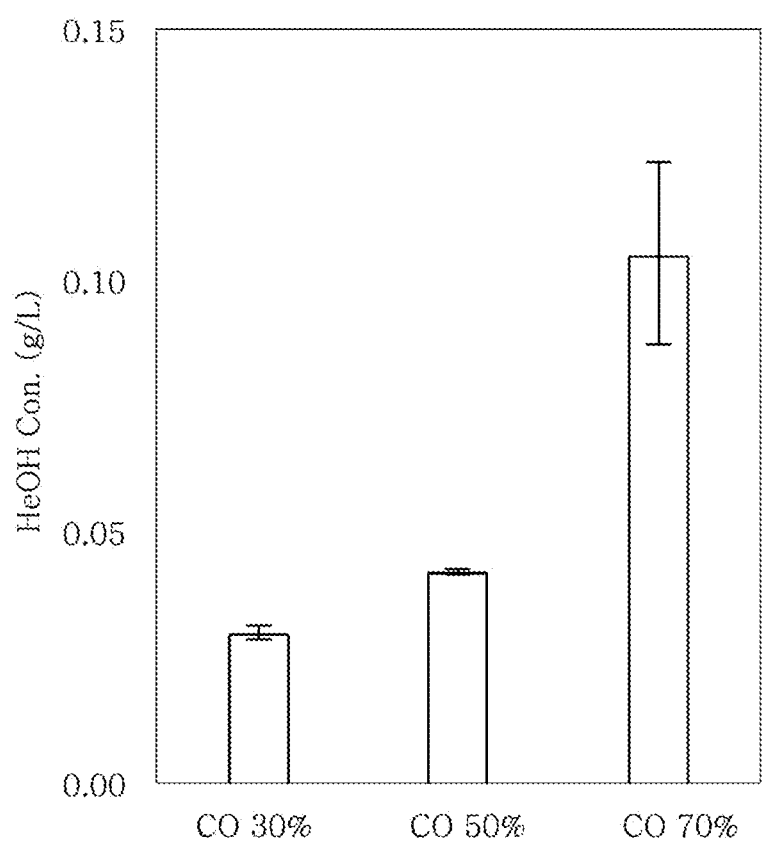

[FIG. 3A]
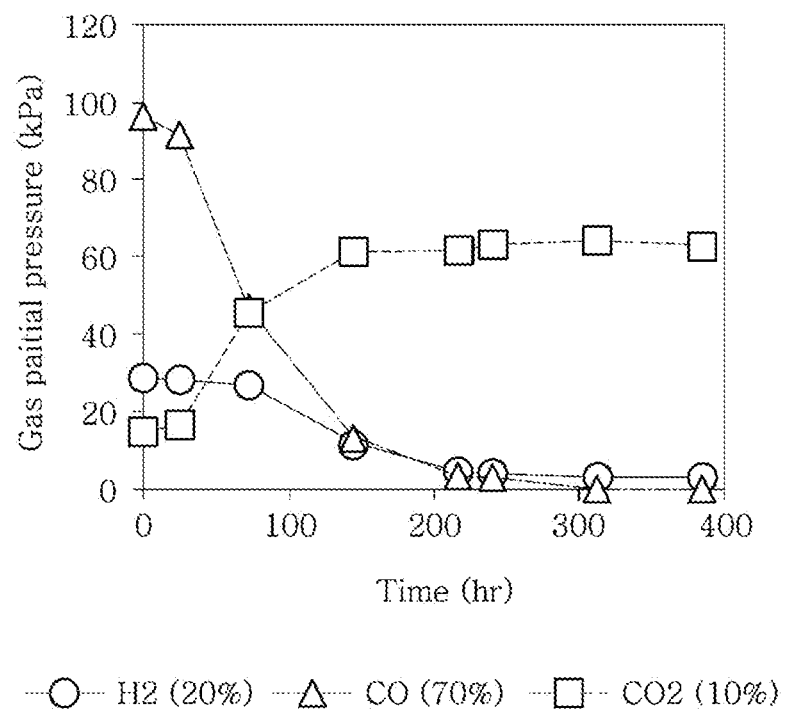

[FIG. 3B]
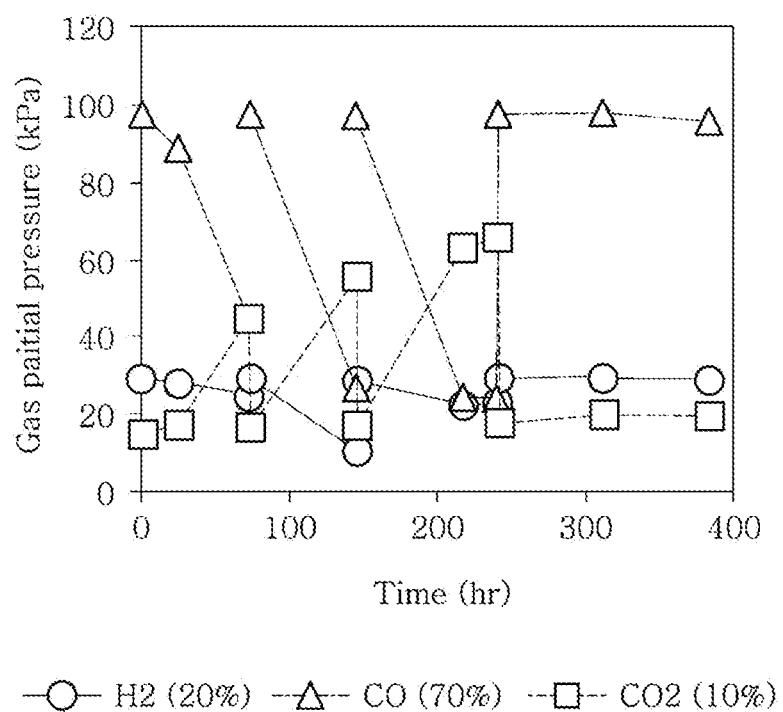

[FIG. 3C]
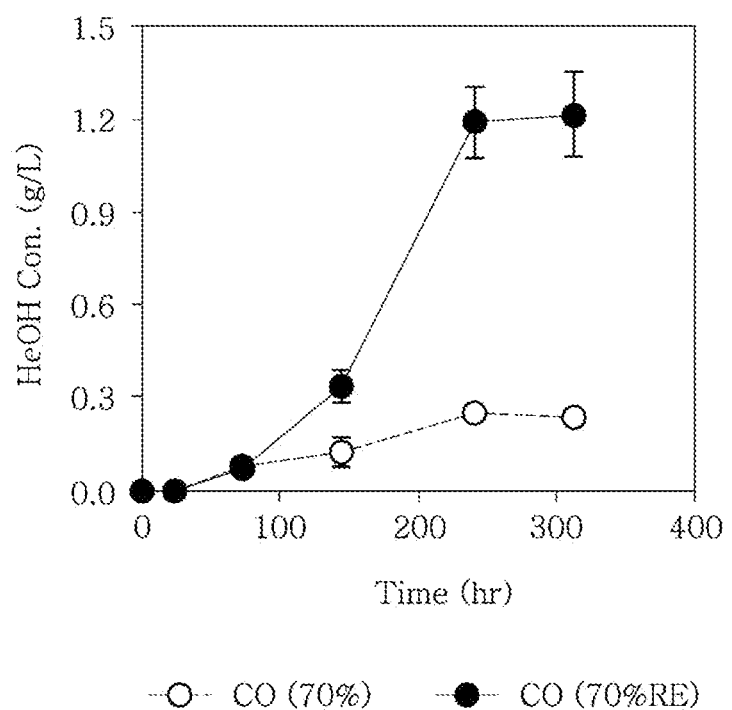

[FIG. 4A]
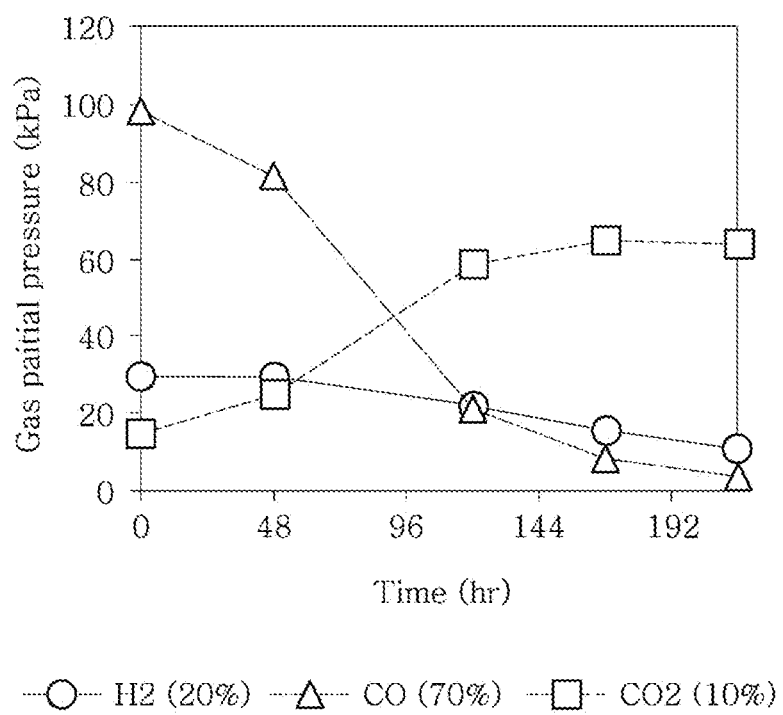

[FIG. 4B]
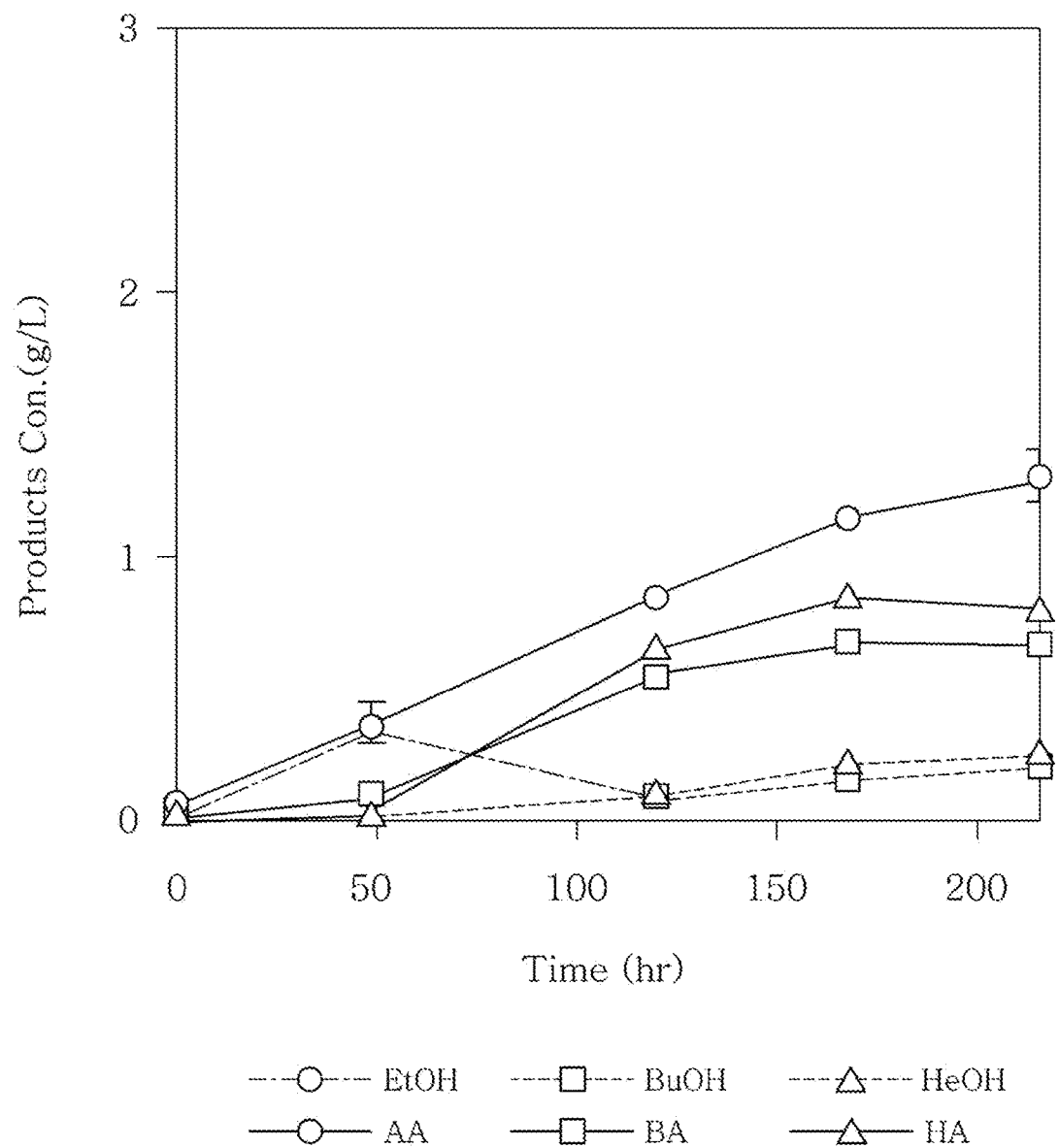

[FIG. 4C]
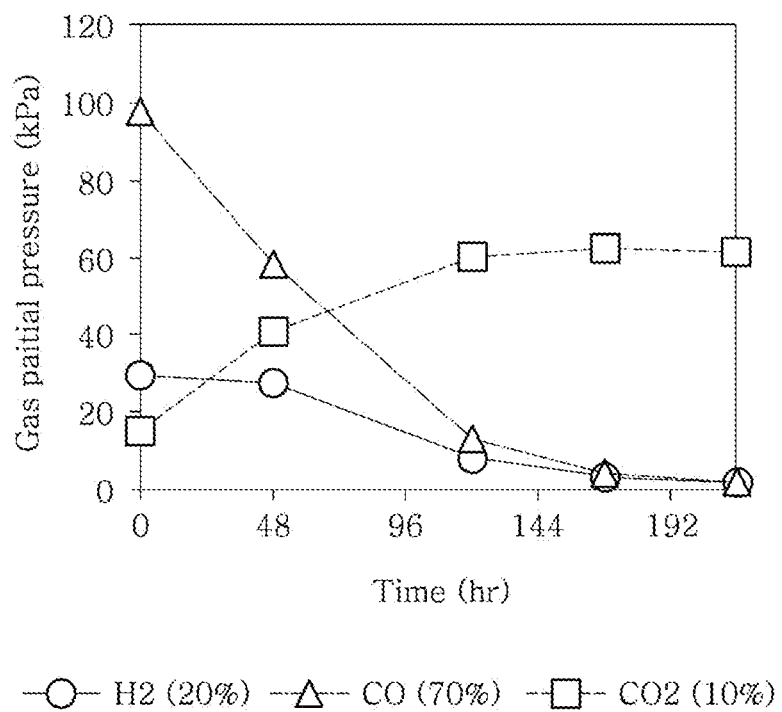

[FIG. 4D]
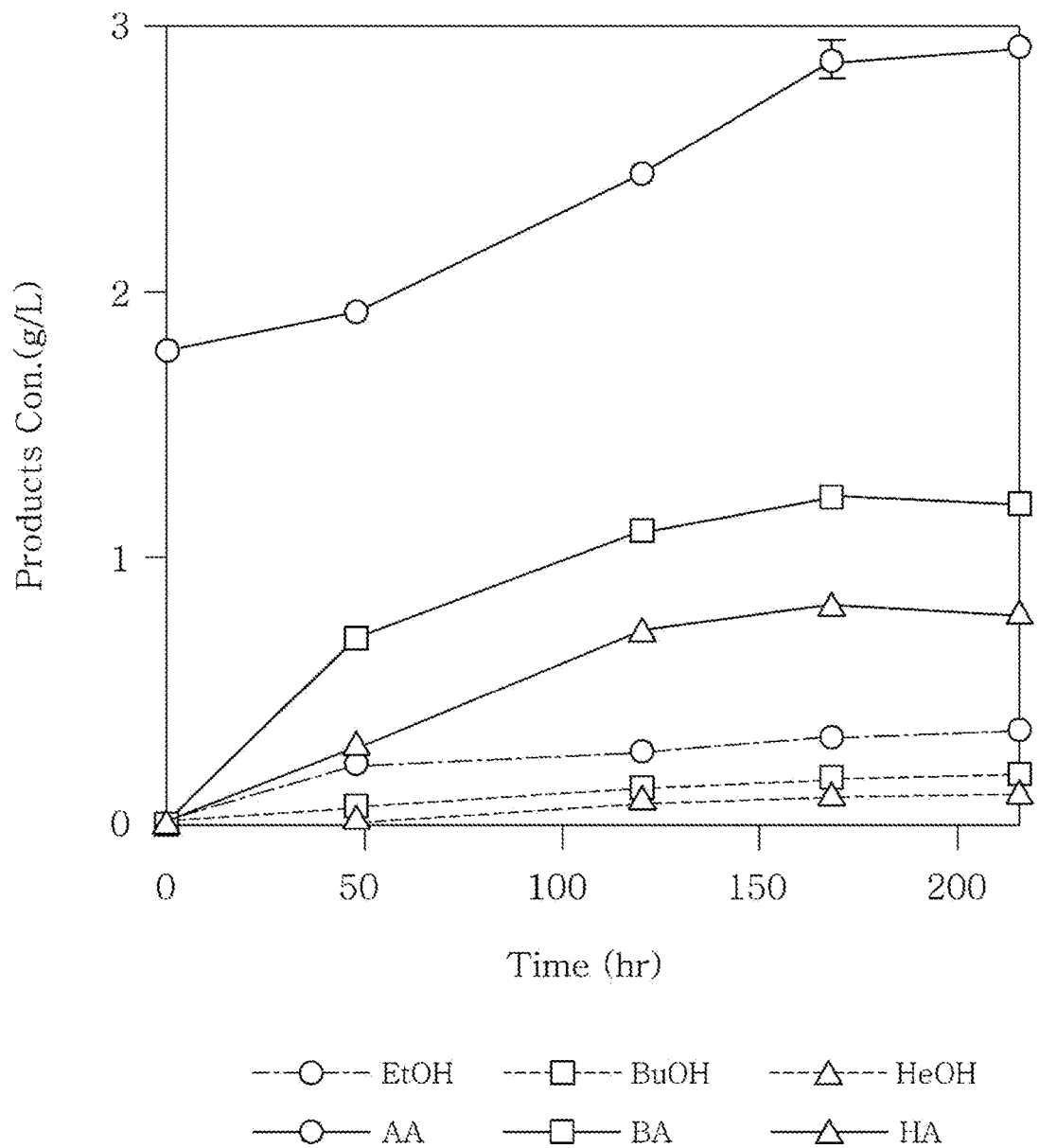

[FIG. 4E]
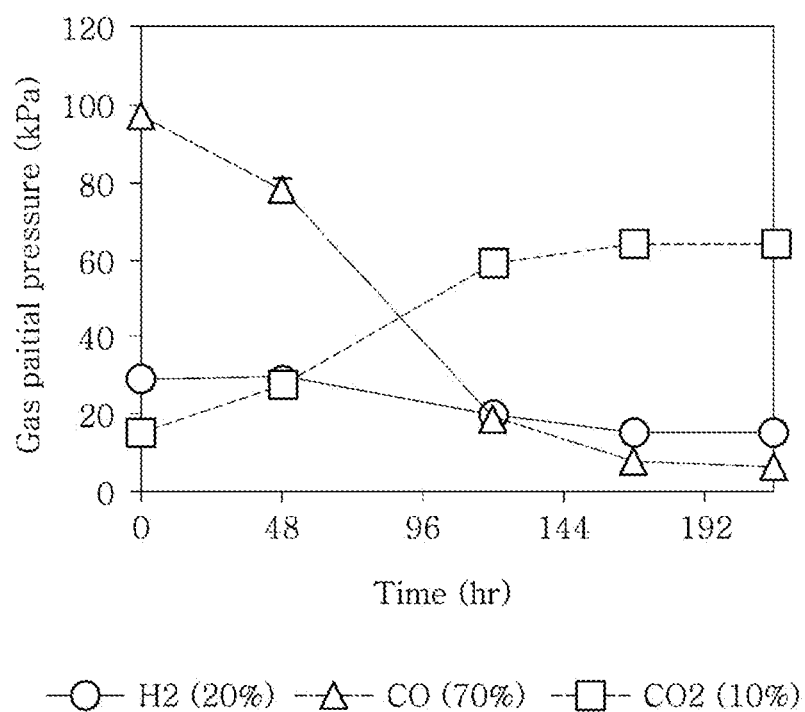

[FIG. 4F]
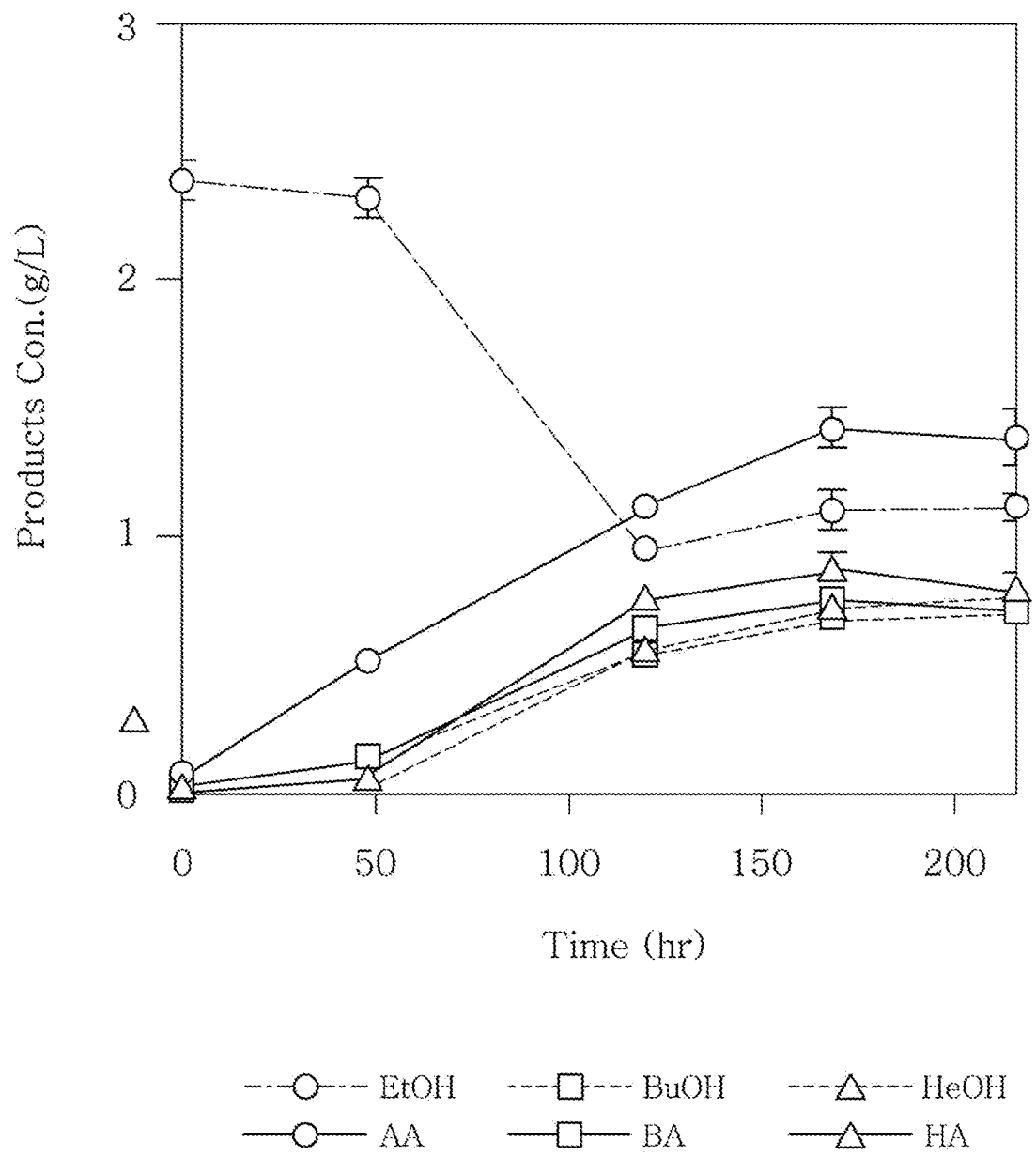

[FIG. 5A]
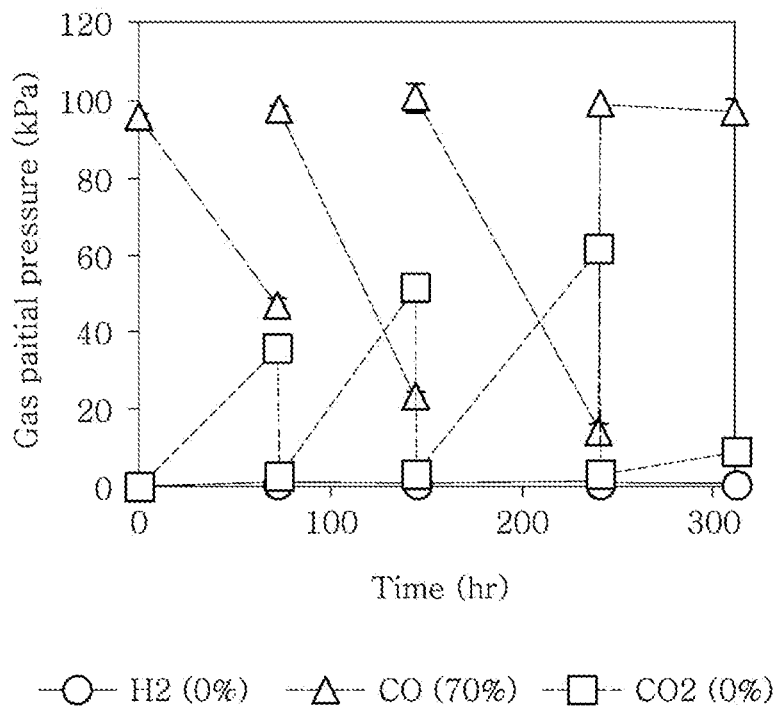
[FIG. 5B]
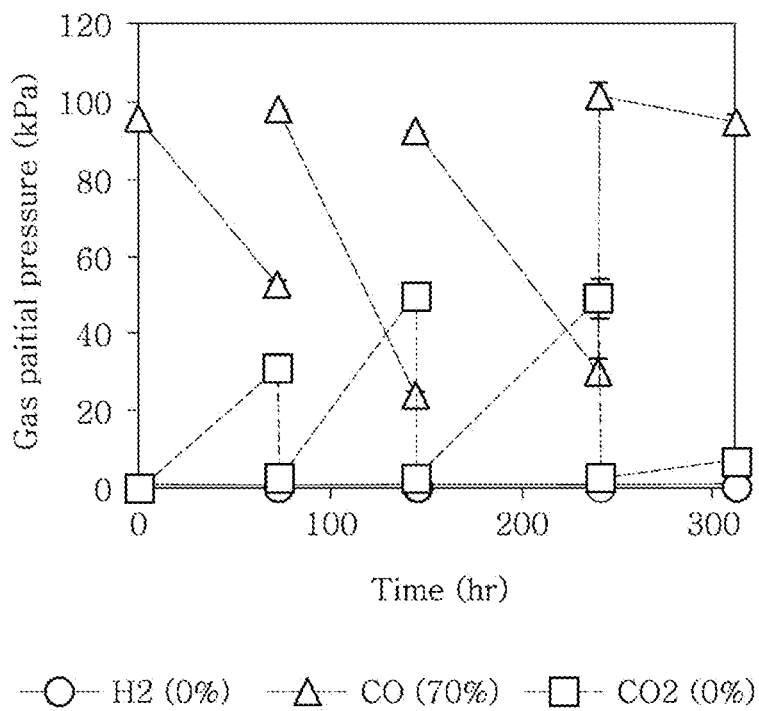

[FIG. 5C]
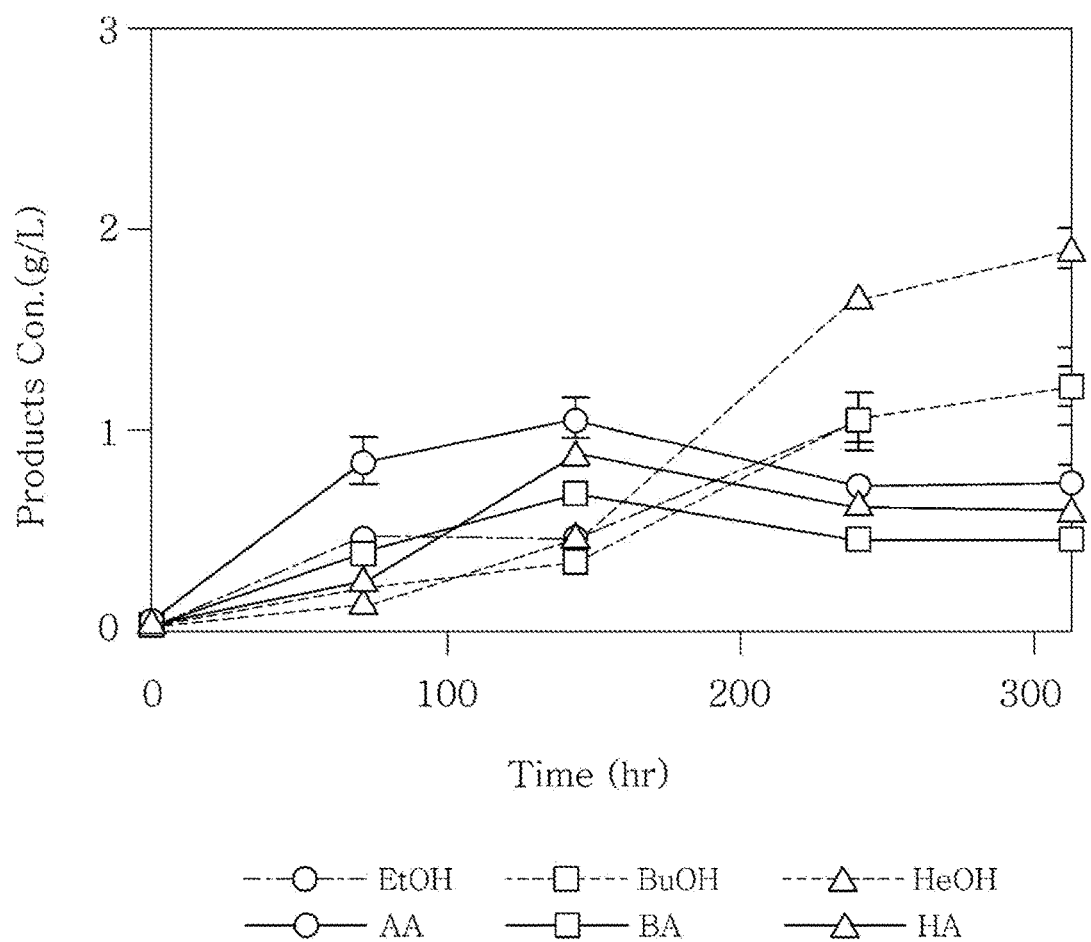

[FIG. 5D]
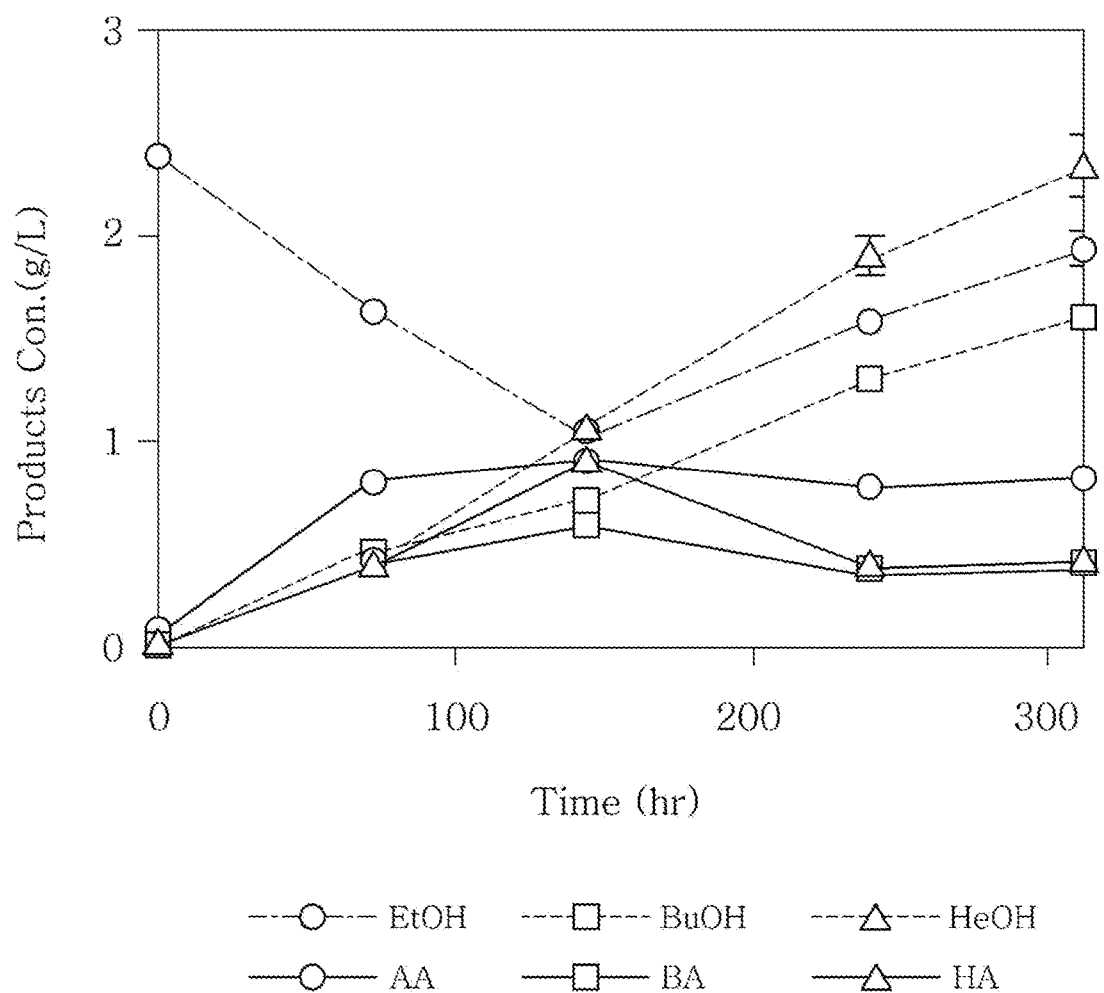

MEDIUM COMPOSITION FOR PRODUCING ALCOHOL FROM SYNTHETIC GAS COMPRISING ETHANOL AND METHOD FOR PRODUCING ALCOHOL USING THE SAME

CROSS-REFERENCE TO RELATED APPLICATION

This application claims priority to Korean Patent Application No. 10-2021-0124831, filed on Sep. 17, 2021, and all the benefits accruing therefrom under U.S.C. § 119, the contents of which in its entirety are herein incorporated by reference.

BACKGROUND

1. Field

The present disclosure relates to a composition for preparing one or more alcohol selected from a group consisting of hexanol and butanol using ethanol and synthesis gas, and a method for preparing the alcohol.

Description about National Support Research and Development

This study is made by the support of the establishment of science and engineering research base (R&D) of the Korea Institute of Science and Technology under the supervision of the National Research Foundation of Korea, and the subject name thereof is Development of high-performance microorganism and fermentation technology for production of 1-hexanol from syngas (Subject Identification No.: 2019R1A6A3A0109499012). This study also is made by the support of the climate change response technology development (R&D) of the Korea Institute of Science and Technology under the supervision of the National Research Foundation of Korea, and the subject name thereof is Development of medium/long-chain fatty acid production strains and bioprocesses for converting unused biomass (Subject Identification No.: 2020M1A2A208084712).

2. Description of the Related Art

A variety of raw materials are produced from petroleum resources through petroleum chemical processes, including not only transport fuels but also synthetic fibers, plastics, etc. The development of renewable energy is required to overcome the limited reservoir of petroleum resources and replace them. The biorefinery technology for production of bioenergy and biocompounds to cope with the resource depletion issue is drawing attentions. The biomass currently used in biorefineries include food biomass such as corn, lignocellulosic biomass, algae, etc. However, the use of food resources has problems that the cost of raw materials accounts for 50% of the total production cost, the cultivation area is limited and loss of carbon sources occurs during the production. For economical production of biofuels and biocompounds, it is necessary to utilize inexpensive carbon sources. In this regard, biofuels using synthesis gas are drawing attentions. Synthesis gas refers to a gas mixture consisting of carbon monoxide (CO), carbon dioxide ($CO_2$) and hydrogen ($H_2$), which is obtained from a gasification process of carbon-based raw materials such as waste, coal, coke, low-grade hydrocarbon gas, naphtha, fuel oil, etc. Carbon monoxide and carbon dioxide produced during utilization of petroleum resources are emitted to the atmosphere and cause global warming. In Korea, about 13 million tons of byproduct gas is generated annually during smelting in steel mills, and 35-40% is emitted to the atmosphere in the form of carbon monoxide. Efforts to reduce carbon dioxide emission through policy operation and technological development are being made in Korea and globally. Conversion of waste gas (including CO and $CO_2$) generated during use of petroleum resources into valuable products can achieve supply of inexpensive raw materials and reduction of carbon dioxide ($CO_2$ fixation) at the same time. Synthesis gas is an affluent, economical and eco-friendly carbon source that can be obtained from CO-containing industrial byproduct gases. Production of valuable materials using the synthesis gas will become a next-generation refinery technology that overcomes the limitation of the biomass-utilizing refinery technologies.

Hexanol is a $C_6$ alcohol that can be used in various applications derived from petrochemistry as a platform material for transport fuels and petrochemicals. Although bioethanol and biobutanol are commercially available as alternatives to transport fuels, $C_6$ alcohols are more suitable as an alternative fuel to gasoline, as compared to ethanol due to more carbon atoms, and have a very large potential for growth as future biofuel materials. In addition, the $C_6$ alcohol can be chemically converted to 1-hexene. 1-Hexene is used for various petrochemical products such as metallocenes, PE, LLDPE, HDEP, alcoholic cleansing agents, synthetic lubricating oils, etc. The global market for 1-hexene is about 2 trillion won with 1 million tons a year. Korea depends entirely on imports for its supplies. Biological production of hexanol from fermentable sugar, rather than from synthesis gas or byproduct gas, is limited due to the cost for supplying a carbon source and insufficient reducing power. In contrast, production of hexanol from synthesis gas or byproduct gas including CO is advantageous owing to sufficient supply of reducing power. The production of hexanol using synthesis gas as an inexpensive carbon source can be an alternative for ensuring competitiveness in the $C_6$ compound market.

Meanwhile, butanol is a $C_4$ alcohol that can replace gasoline as a fuel material together with ethanol. Due to physical properties very similar to that of gasoline and higher energy density than ethanol with two more carbon atoms, it has many advantages over ethanol. When compared with ethanol, the $C_4$ alcohol can be used without any treatment because it does not corrode the petrochemical infrastructure through mutual dissolution with water. In addition, it has higher combustion efficiency than ethanol, can be added at high concentration due to excellent miscibility with gasoline and does not require engine calibration. Furthermore, it can be supplied with the conventional gasoline supply line due to low vapor pressure.

It is known that Clostridia produce organic acids and alcohols using various carbon sources (starch, disaccharides, hexoses, pentoses, glycerol, cellulose and syngas). Among them, the microorganisms that produce acetic acid through anaerobic metabolism of synthesis gas or sugar as sources of carbon and energy are called acetogens. Acetogens have the Wood-Ljungdahl pathway. The acetogens mainly produce $C_2$ compounds after biosynthesis of acetyl-CoA using carbon dioxide or carbon monoxide through the Wood-Ljungdahl pathway. Although it is known that some strains of acetogens can also produce $C_4$ and $C_6$ compounds, there are only a handful of them. As acetogens among the anaerobic microorganisms using synthesis gas, *Acetobacterium woodii, Clostridium aceticum, Clostridium autoethanogenum, Clostridium ljungdahlii, Clostridium carboxidivorans, Clostridium ragsdalei, Clostridium kluyveri, Eubacterium*

*limosum, Peptostreptococcus productus, Butyribacterium methylotrophicum, Clostridium drakei*, etc. are well known. Among them, *C. carboxidivorans* P7 (DSMZ 15243) is reported to be capable of producing $C_2$-$C_6$ compounds.

First, when the microorganisms ferment a sugar, it is converted to acetyl-CoA via pyruvate through glycolysis, and acetic acid, ethanol, butyric acid, etc. are synthesized from acetyl-CoA. Professor Liao's research team at UCLA produced mg/L hexanol using genetically modified *Escherichia coli*. However, this method is sugar-based and the concentration of hexanol produced is very low (Dekishima, Y, Lan, E. I., Shen, C. R., Cho, K. M., Liao, J. C. 2011. Extending Carbon Chain Length of 1-Butanol Pathway for 1-Hexanol Synthesis from Glucose by Engineered *Escherichia coli*. *Journal of the American Chemical Society*, 133 (30), 11399-11401). Dellomonaco et al. (Dellomonaco, C., Clomburg, J. M., Miller, E. N., Gonzalez, R. 2011. Engineered reversal of the β-oxidation cycle for the synthesis of fuels and chemicals. *Nature*, 476, 355) produced 0.21 g/L $C_6$ alcohol through the inverse reaction of beta-oxidation cycle. The sugar-based hexanol production shows very limited hexanol concentration because sufficient reducing power necessary for hexanol production cannot be supplied.

Production of hexanol using *Clostridium carboxidivorans* P7, which is known as an acetogen that produces hexanol from synthesis gas, was reported. 0.94 g/L $C_6$ alcohol was produced through fermentation for 335 hours using wild-type *Clostridium carboxidivorans* P7 by optimizing medium condition and fermentation condition (Phillips, J. R., Atiyeh, H. K., Tanner, R. S., Torres, J. R., Saxena, J., Wilkins, M. R., Huhnke, R. L. 2015. Butanol and hexanol production in *Clostridium carboxidivorans* syngas fermentation: Medium development and culture techniques. *Bioresource Technology*, 190, 114-121.). Ramió-Pujol et al. (Ramió-Pujol, S., Ganigué, R., Bañeras, L., Colprim, J. 2015. Incubation at 25 C prevents acid crash and enhances alcohol production in *Clostridium carboxidivorans* P7. *Bioresource technology*, 192, 296-303.) produced 0.84 g/L hexanol at low temperature (25° C.). Han et al. (Han, Y-F., Xie, B.-T., Wu, G.-x., Guo, Y-Q., Li, D.-M., Huang, Z.-Y. 2020. Combination of Trace Metal to Improve Solventogenesis of *Clostridium carboxidivorans* P7 in Syngas Fermentation. *Frontiers in Microbiology*, 11(2376)) produced 0.3 g/L hexanol from synthesis gas by supplying Mo at low concentration. Shen et al. (Shen, S., Wang, G., Zhang, M., Tang, Y, Gu, Y, Jiang, W., Wang, Y, Zhuang, Y. 2020. Effect of temperature and surfactant on biomass growth and higher-alcohol production during syngas fermentation by *Clostridium carboxidivorans* P7. *Bioresources and Bioprocessing*, 7(1), 56) produced 0.66 g/L hexanol by changing temperature during culturing of microorganisms. The production of hexanol from synthesis gas exhibits higher productivity than that from sugar. It is because the supply of reducing power required for hexanol production during metabolism is insufficient for sugar as compared to CO. But, the productivity of hexanol production from synthesis gas is also very low, and varies greatly depending on medium composition and culturing condition. In addition, the utilization efficiency of carbon source is very low because $C_2$ and $C_4$ organic acids and alcohols are produced together with hexanol. The productivity of hexanol production should be improved to ensure the economic efficiency of hexanol production. For this, the culturing condition should be optimized.

Meanwhile, production of butanol through fermentation has the problem that concentration, yield, productivity, etc. is very low because the butanol-producing microorganisms are inhibited by the produced butanol. Efforts are being made to overcome this, including the development or genetic manipulation of butanol-resistant microorganisms (e.g., *Clostridium beijerinckii* NCIMB 8052), and improvement of the concentration and yield of butanol through separation, purification, etc. Professor Liao's research team at UCLA developed butanol-producing *E. coli* using metabolic engineering (S. Atsumi, T. Hanai, and J. C. Liao, *Nature*, 451, 86 (2008)). But, the concentration of the alcohol produced with the *E. coli* developed by the Professor Liao's team is only 0.01-0.9 g/L, which is much lower than that of ethanol (50-100 g/L) or butanol (10-15 g/L). Such a low concentration results in cost increase because the separation/purification process becomes difficult. For the production of biofuels in large quantities, the improvement of productivity through high-concentration culturing is essential. In addition, for the microorganisms that produce butanol through acetone-butanol-ethanol (ABE) fermentation (typically *Clostridium acetobutylicum*), pH is decreased during the early stage of fermentation due to acid production and, the ABE solvent is produced due to the decreased pH. Furthermore, the ABE fermentation by *Clostridium acetobutylicum*, etc. using fermentable sugar has the problem that butanol production yield is low and there is difficulty in separating the produced butanol because acetone is produced as a byproduct up to about 50% of the butanol concentration.

Therefore, the inventors of the present disclosure have researched on production of hexanol through fermentation of gas using a wild-type *Clostridium carboxidivorans* P7 acetogen strain (*C. carboxidivorans* P7). Firstly, they aimed at optimizing the culturing condition for improved hexanol production. Because the products produced by the acetogen strain and the productivity thereof are changed depending on the culturing condition, they intended to optimize the culturing condition for hexanol production. Secondly, they intended to improve hexanol productivity and allow effective utilization of a carbon source by providing reducing power, which is essential in hexanol production, using ethanol.

DISCLOSURE

Technical Problem

Although the production of $C_2$ or higher materials using synthesis gas has previously been reported for other strains, there is limitation in that the productivity is very low. In particular, the existing method of producing hexanol by fermenting sugar has the limitation that the hexanol production amount is very small because enough reducing power is not supplied for the hexanol production. And, the existing technology of producing hexanol from synthesis gas also has the problem that hexanol is produced at very low concentration. In addition, the existing method of producing butanol by fermenting sugar has the problem that the butanol production is inhibited by the produced butanol or the production yield, productivity, etc. of butanol are low because acetone is produced as a byproduct.

However, the present disclosure improves the productivity of $C_4$ and $C_6$ alcohols, which are valuable materials, by optimizing a fermentation process and maximizes the production of $C_4$ and $C_6$ alcohols by adding ethanol. As a result, the productivity of $C_4$ and $C_6$ alcohols is maximized by adding ethanol during the early stage of fermentation and further adding synthesis gas.

Accordingly, the present disclosure is directed to improving the productivity alcohol production by a strain producing one or more alcohol selected from a group consisting of hexanol and butanol by optimizing the fermentation condition of a fermentation process such as culturing temperature, gas supply method, etc. and supplying reducing power necessary for the alcohol production by adding ethanol. In addition, the present disclosure is directed to improving alcohol production from synthesis gas for economical and effective production of the alcohol by adding ethanol.

Technical Solution

In an aspect, the present disclosure provides a medium composition for preparing an alcohol, wherein the alcohol is one or more alcohol selected from a group consisting of hexanol and butanol, the composition contains ethanol as an active ingredient, the alcohol is prepared from synthesis gas, and the composition is for culturing a strain producing the alcohol.

In another aspect, the present disclosure provides a method for preparing an alcohol, which includes: a step of inoculating an alcohol-producing strain to a medium containing the composition; and a step of supplying synthesis gas to the medium.

Advantageous Effects

A medium composition according to an aspect of the present disclosure contains ethanol as an active ingredient. By culturing a strain producing one or more alcohol selected from a group consisting of hexanol and butanol in a medium containing the composition and supplying synthesis gas, hexanol or butanol can be prepared economically using inexpensive synthesis gas. Hexanol or butanol can be produced with high efficiency by focusing the flow of the carbon source consumed in the fermentation process to the production of hexanol or butanol.

DESCRIPTION OF DRAWINGS

FIGS. 1A-1E show the change in synthesis gas by *C. carboxidivorans* P7 depending on temperature (FIG. 1A, 30° C.; FIG. 1B, 33° C.; FIG. 1C, 37° C.), hexanol production amount after fermentation (FIG. 1D), and products produced after culturing and fermentation at 30° C. (FIG. 1E).

FIGS. 2A and 2B show the consumption of synthesis gas by *C. carboxidivorans* P7 depending on the supply amount of carbon monoxide (FIG. 2A; CO 30%, CO:Ar=30:70; CO 50%, CO:Ar=50:50; CO 70%, CO:Ar=70:30) and hexanol production amount depending on the supply amount of carbon monoxide (FIG. 2B).

FIGS. 3A-3C show the consumption of synthesis gas and hexanol production by *C. carboxidivorans* P7 depending on additional supply of synthesis gas. FIG. 3A shows the consumption of synthesis gas when it is not supplied additionally after the first supply of synthesis gas ($CO:CO_2:H_2$=70:10:20), FIG. 3B shows the consumption of synthesis gas when synthesis gas is supplied additionally ($CO:CO_2:H_2$=70:10:20), and FIG. 3C compares hexanol production depending on the additional supply of synthesis gas.

FIGS. 4A-4D show the consumption of synthesis gas and production of products by *C. carboxidivorans* P7 depending on addition of acetic acid. FIGS. 4A and 4B show the consumption of synthesis gas (FIG. 4A) and production of products (FIG. 4B) when only synthesis gas is supplied, and FIGS. 4C and 4D show the consumption of synthesis gas (FIG. 4C) and production of products (FIG. 4D) when 2 g/L sodium acetate is added.

FIGS. 4E and 4F show the consumption of synthesis gas and production of products by *C. carboxidivorans* P7 depending on addition of ethanol. FIG. 4E shows the consumption of synthesis gas when 2 g/L ethanol is supplied, and FIG. 4F shows the production of products.

FIGS. 5A-5D show the consumption of synthesis gas and production of products by *C. carboxidivorans* P7 depending on addition of ethanol during additional supply of synthesis gas. FIGS. 5A and 5C show the consumption of synthesis gas (FIG. 5A) and production of products (FIG. 5C) when only synthesis gas is supplied additionally, and FIGS. 5B and 5D show the consumption of synthesis gas (FIG. 5B) and production of products (FIG. 5D) when ethanol is added during the early stage of fermentation by additionally supplying synthesis gas.

BEST MODE

Hereinafter, the present disclosure is described in detail.

In an aspect, the present disclosure provides a medium composition for preparing an alcohol, wherein the alcohol is one or more alcohol selected from a group consisting of hexanol and butanol, the composition contains ethanol as an active ingredient, the alcohol is prepared from synthesis gas, and the composition is for culturing a strain producing the alcohol.

In an aspect of the present disclosure, the alcohol is an alcohol selected from a group consisting of hexanol and butanol.

In an aspect of the present disclosure, the medium composition for preparing an alcohol may contain ethanol as an active ingredient. Ethanol is a major product of acetogen strains using synthesis gas, together with acetic acid. For production of alcohols, acetogen strains consume the reducing power produced during the metabolism of synthesis gas. By allowing the reducing power consume during ethanol production consume during the metabolism of synthesis gas to be used for production of hexanol or butanol and supplying sufficient reducing power for hexanol or butanol production, the productivity of hexanol or butanol production can be improved. The composition according to an aspect of the present disclosure can provide economical advantage because the productivity of hexanol or butanol production can be improved using ethanol.

In an aspect of the present disclosure, the ethanol may be contained in an amount of 0.2-20 g/L based on the total volume of a medium in which the medium composition is contained. Specifically, the ethanol may be contained in an amount of 0.2 g/L or more, 0.4 g/L or more, 0.6 g/L or more, 0.8 g/L or more, 1 g/L or more, 1.1 g/L or more, 1.2 g/L or more, 1.3 g/L or more, 1.4 g/L or more, 1.5 g/L or more, 1.6 g/L or more, 1.7 g/L or more, 1.8 g/L or more, 1.9 g/L or more, 2 g/L or more, 3 g/L or more, 4 g/L or more, 5 g/L or more, 6 g/L or more, 7 g/L or more, 8 g/L or more, 9 g/L or more, 10 g/L or more or 15 g/L or more, and 20 g/L or less, 18 g/L or less, 16 g/L or less, 14 g/L or less, 12 g/L or less, 10 g/L or less, 8 g/L or less, 6 g/L or less, 5 g/L or less, 4 g/L or less, 3 g/L or less, 2.9 g/L or less, 2.8 g/L or less, 2.7 g/L or less, 2.6 g/L or less, 2.5 g/L or less, 2.4 g/L or less, 2.3 g/L or less, 2.2 g/L or less, 2.1 g/L or less, 2 g/L or less, 1 g/L or less or 0.5 g/L or less, based on the total volume of a medium in which the medium composition is contained. However, the amount of the ethanol is not limited thereto as long as hexanol or butanol can be produced without inhibiting the growth of the microorganism.

In an aspect of the present disclosure, the strain producing the alcohol may be a strain capable of producing a $C_4$ or higher alcohol, specifically a strain producing one or more alcohol selected from a group consisting of hexanol and butanol, more specifically an acetogen strain. Acetogen strains utilizing synthesis gas convert the synthesis gas to various materials (ethanol, acetic acid, butyric acid, butanol, etc.) through the Wood-Ljungdahl pathway. It is known that, among the acetogen strains, *Clostridium carboxidivorans* P7 and *Clostridium* ragsdalei can produce $C_4$ or higher alcohols. However, for production of hexanol or butanol for industrial use, productivity should be improved first because the production amount is very small.

In another aspect of the present disclosure, the strain producing the alcohol may be one or more selected from a group consisting of *Clostridium carboxidivorans* and *Clostridium* ragsdalei, specifically *Clostridium carboxidivorans*, more specifically *Clostridium carboxidivorans* P7, although any strain can be used as long as it can produce hexanol or butanol using synthesis gas. It has been reported that the *Clostridium carboxidivorans* P7 can produce hexanol using synthesis gas. According to an exemplary embodiment of the present disclosure, hexanol or butanol may be prepared with high efficiency by additionally supplying ethanol during fermentation by the strain using synthesis gas.

The composition according to an aspect of the present disclosure may be for preparation of a $C_4$ or higher alcohol, specifically one or more alcohol selected from a group consisting of hexanol and butanol from synthesis gas. That is to say, the alcohol may be prepared from synthesis gas. More specifically, the synthesis gas may include carbon monoxide and, further more specifically, it may include one or more selected from a group consisting of carbon monoxide, carbon dioxide and hydrogen. The synthesis gas may be used by anaerobic strains having the Wood-Ljungdahl pathway. The strains using synthesis gas are classified as acetogens. The strains classified as acetogens convert synthesis gas to acetyl-CoA through the Wood-Ljungdahl pathway. Microorganisms produce acetic acid from acetyl-CoA in order to obtain ATP necessary for growth, and acetogens having the metabolic pathway of producing ethanol and $C_4$-$C_6$ organic acids and alcohols produce $C_2$-$C_6$ organic acids and alcohols. In an example according to the present disclosure, it was confirmed that hexanol or butanol can be produced from synthesis gas with high efficiency using an acetogen, specifically a strain capable of producing hexanol, by optimizing culturing temperature, supplying synthesis gas, adding ethanol, etc. (Test Examples 1-5).

In an aspect of the present disclosure, the synthesis gas may be supplied additionally. Specifically, the synthesis gas may be supplied additionally such that carbon monoxide in the synthesis gas is not consumed completely. More specifically, it may be supplied additionally such that carbon monoxide is present above 0 kPa, further more specifically 1 kPa or higher, even more specifically 1 kPa or higher, 1.2 kPa or higher, 1.4 kPa or higher, 1.6 kPa or higher, 1.8 kPa or higher, 2 kPa or higher, 2.2 kPa or higher, 2.4 kPa or higher, 2.6 kPa or higher, 2.8 kPa or higher, 3 kPa or higher, 3.2 kPa or higher, 3.4 kPa or higher, 3.6 kPa or higher, 3.8 kPa or higher, 4 kPa or higher, 4.2 kPa or higher, 4.4 kPa or higher, 4.6 kPa or higher, 4.8 kPa or higher, 5 kPa or higher, 6 kPa or higher, 7 kPa or higher, 8 kPa or higher, 9 kPa or higher, 10 kPa or higher, 12 kPa or higher, 14 kPa or higher, 16 kPa or higher, 18 kPa or higher, 20 kPa or higher, 22 kPa or higher, 24 kPa or higher, 26 kPa or higher, 28 kPa or higher or 30 kPa or higher. The additional supply of synthesis gas may be performed 1 or more times, 2 or more times, 3 or more times, 4 or more times, 5 or more times, 6 or more times, 7 or more times, 8 or more times, 9 or more times, 10 or more times, 12 or more times, 14 or more times, 16 or more times, 18 or more times, 20 or more times, 25 or more times, 30 or more times, 40 or more times or 40 or more times. However, the number of addition is not limited as long as the desired amount of hexanol or butanol can be produced. In an example according to the present disclosure, it was confirmed that the hexanol production amount is increased by about 5.3 times when synthesis gas is supplied additionally as compared to when it is not supplied additionally (Test Example 3).

In an aspect of the present disclosure, the supply amount of synthesis gas may be 0.3-7.5 bar, specifically 0.3 bar or higher, 0.4 bar or higher, 0.5 bar or higher, bar or higher, 0.7 bar or higher, 0.8 bar or higher, 0.9 bar or higher, 1 bar or higher, 1.1 bar or higher, 1.2 bar or higher, 1.3 bar or higher, 1.4 bar or higher, 1.5 bar or higher, 1.6 bar or higher, 1.8 bar or higher, 2 bar or higher, 4 bar or higher or 6 bar or higher, and 7.5 bar or lower, 6 bar or lower, 4 bar or lower, 3 bar or lower, 2.8 bar or lower, 2.6 bar or lower, 2.4 bar or lower, 2.2 bar or lower, 2 bar or lower, 1.9 bar or lower, 1.8 bar or lower, 1.7 bar or lower, 1.6 bar or lower, 1.5 bar or lower, 1.3 bar or lower, 1.2 bar or lower, 1 bar or lower or 0.5 bar or lower. However, the supply amount of synthesis gas is not limited as long as the carbon source necessary for the growth of the microorganism can be supplied and hexanol or butanol can be produced without inhibiting the growth of the microorganism.

In an aspect of the present disclosure, the alcohol may be prepare at 25-37° C., specifically at 25° C. or higher, 26° C. or higher, 27° C. or higher, 28° C. or higher, 29° C. or higher, 30° C. or higher, 31° C. or higher, 32° C. or higher, 33° C. or higher, 34° C. or higher, 35° C. or higher or 36° C. or higher, and 37° C. or lower, 36° C. or lower, ° C. or lower, 34° C. or lower, 33° C. or lower, 32° C. or lower, 31° C. or lower, 30° C. or lower, 29° C. or lower, 28° C. or lower, 27° C. or lower or 26° C. or lower. However, the temperature is not limited as long as the growth of the microorganism is not inhibited and hexanol or butanol can be produced using ethanol by supplying synthesis gas. In an example according to the present disclosure, it was confirmed that the productivity of hexanol production is higher as the culturing temperature is lower and, when considering the metabolic rate of the microorganism, etc., hexanol can be produced with high efficiency by culturing at 25-37° C., specifically at 30° C. (Test Example 1).

In another aspect, the present disclosure provides a step of inoculating an alcohol-producing strain to a medium containing the medium composition for preparing an alcohol, which contains ethanol as an active ingredient, is for preparing one or more alcohol selected from a group consisting of hexanol and butanol from synthesis gas and is for culturing the alcohol-producing strain; and a step of supplying synthesis gas to the medium. The ethanol, the amount of the ethanol, the alcohol, the alcohol-producing strain, the preparation of the alcohol, the synthesis gas, etc. are the same as described above.

In an aspect of the present disclosure, the supply amount of synthesis gas may be 0.3-7.5 bar, specifically 0.3 bar or higher, 0.4 bar or higher, 0.5 bar or higher, bar or higher, 0.7 bar or higher, 0.8 bar or higher, 0.9 bar or higher, 1 bar or higher, 1.1 bar or higher, 1.2 bar or higher, 1.3 bar or higher, 1.4 bar or higher, 1.5 bar or higher, 1.6 bar or higher, 1.8 bar or higher, 2 bar or higher, 4 bar or higher or 6 bar or higher, and 7.5 bar or lower, 6 bar or lower, 4 bar or lower, 3 bar or lower, 2.8 bar or lower, 2.6 bar or lower, 2.4 bar or lower, 2.2 bar or lower, 2 bar or lower, 1.9 bar or lower, 1.8 bar or lower, 1.7 bar or lower, 1.6 bar or lower, 1.5 bar or lower, 1.3 bar or lower, 1.2 bar or lower, 1 bar or lower or 0.5 bar or lower. However, the supply amount of synthesis gas is not limited as long as the carbon source necessary for the growth of the microorganism can be supplied and hexanol or butanol can be produced without inhibiting the growth of the microorganism.

In an aspect of the present disclosure, the synthesis gas may include carbon monoxide at, based on the total pressure of the supplied gas or supplied synthesis gas, 10-100%. Specifically, the proportion of carbon monoxide may be, based on the total pressure of the supplied gas or supplied synthesis gas, 10% or higher, 15% or higher, 20% or higher, 25% or higher, 30% or higher, 35% or higher, 40% or higher, 45% or higher, 50% or higher, 55% or higher, 60% or higher, 62% or higher, 64% or higher, 66% or higher, 68% or higher, 70% or higher, 75% or higher, 80% or higher, 85% or higher, 90% or higher or 95% or higher, and 100% or lower, 99% or lower, 95% or lower, 90% or lower, 85% or lower, 80% or lower, 78% or lower, 76% or lower, 74% or lower, 72% or lower, 70% or lower, 65% or lower, 60% or lower, 55% or lower, 50% or lower, 45% or lower, 40% or lower, 35% or lower, 30% or lower, 25% or lower, 20% or lower or 15% or lower. However, the proportion of carbon monoxide is not limited as long as the carbon source necessary for the growth of the microorganism can be supplied and hexanol or butanol can be produced without inhibiting the growth of the microorganism.

Alternatively, in an aspect of the present disclosure, the supply amount of carbon monoxide may be 1-750 kPa, specifically 1 kPa or higher, 5 kPa or higher, 10 kPa or higher, 15 kPa or higher, 20 kPa or higher, 25 kPa or higher, 30 kPa or higher, 35 kPa or higher, 40 kPa or higher, 45 kPa or higher, 50 kPa or higher, 55 kPa or higher, 60 kPa or higher, 62 kPa or higher, 64 kPa or higher, 66 kPa or higher, 68 kPa or higher, 70 kPa or higher, 75 kPa or higher, 80 kPa or higher, 85 kPa or higher, 90 kPa or higher, 95 kPa or higher, 100 kPa or higher, 200 kPa or higher, 300 kPa or higher, 400 kPa or higher, 500 kPa or higher, 600 kPa or higher or 700 kPa or higher, and 750 kPa or lower, 700 kPa or lower, 600 kPa or lower, 500 kPa or lower, 400 kPa or lower, 300 kPa or lower, 200 kPa or lower, 100 kPa or lower, 99 kPa or lower, 95 kPa or lower, 90 kPa or lower, 85 kPa or lower, 80 kPa or lower, 78 kPa or lower, 76 kPa or lower, 74 kPa or lower, 72 kPa or lower, 70 kPa or lower, 65 kPa or lower, 60 kPa or lower, 55 kPa or lower, 50 kPa or lower, 45 kPa or lower, 40 kPa or lower, 35 kPa or lower, 30 kPa or lower, 25 kPa or lower, 20 kPa or lower, 15 kPa or lower, 10 kPa or lower or 5 kPa or lower. However, the supply amount of carbon monoxide is not limited as long as the carbon source necessary for the growth of the microorganism can be supplied and hexanol or butanol can be produced without inhibiting the growth of the microorganism.

In an example according to the present disclosure, it was confirmed that carbon monoxide is consumed rapidly without inhibition by carbon monoxide even when the supply amount of carbon monoxide is increased, suggesting that the hexanol production amount is increased as the amount of supplied carbon monoxide is increased (Test Example 2).

In an aspect of the present disclosure, the step of supplying synthesis gas may be supplying synthesis gas additionally. Specifically, it may be supplied additionally such that carbon monoxide is present in the synthesis gas during the production of hexanol or culturing of the strain. More specifically, it may be supplied additionally such that carbon monoxide is present above 0 kPa. Further more specifically, it may be supplied additionally such that carbon monoxide is present at 1 kPa or higher. Even more specifically, it may be supplied additionally such that carbon monoxide is present at 1 kPa or higher, 1.2 kPa or higher, 1.4 kPa or higher, 1.6 kPa or higher, 1.8 kPa or higher, 2 kPa or higher, 2.2 kPa or higher, 2.4 kPa or higher, 2.6 kPa or higher, 2.8 kPa or higher, 3 kPa or higher, 3.2 kPa or higher, 3.4 kPa or higher, 3.6 kPa or higher, 3.8 kPa or higher, 4 kPa or higher, 4.2 kPa or higher, 4.4 kPa or higher, 4.6 kPa or higher, 4.8 kPa or higher, 5 kPa or higher, 6 kPa or higher, 7 kPa or higher, 8 kPa or higher, 9 kPa or higher, 10 kPa or higher, 12 kPa or higher, 14 kPa or higher, 16 kPa or higher, 18 kPa or higher, 20 kPa or higher, 22 kPa or higher, 24 kPa or higher, 26 kPa or higher, 28 kPa or higher or 30 kPa or higher. The additional supply of synthesis gas may be performed 1 or more times, 2 or more times, 3 or more times, 4 or more times, 5 or more times, 6 or more times, 7 or more times, 8 or more times, 9 or more times, 10 or more times, 12 or more times, 14 or more times, 16 or more times, 18 or more times, 20 or more times, 25 or more times, 30 or more times, 40 or more times or 40 or more times. However, the number of supply is not limited as long as the synthesis gas is supplied to achieve the desired production amount of hexanol or butanol. In an example according to the present disclosure, it was confirmed that the hexanol production amount is increased by about 5.3 times when the synthesis gas is supplied additionally after initial supply as compared to when it is not supplied additionally (Test Example 3).

In an aspect of the present disclosure, the preparation of the alcohol or the culturing of the strain may be performed at 25-37° C. Specifically, the preparation of the alcohol or the culturing of the strain may be performed at 25° C. or higher, 26° C. or higher, 27° C. or higher, 28° C. or higher, 29° C. or higher, 30° C. or higher, 31° C. or higher, 32° C. or higher, 33° C. or higher, 34° C. or higher, 35° C. or higher or 36° C. or higher, and 37° C. or lower, 36° C. or lower, 35° C. or lower, 34° C. or lower, 33° C. or lower, 32° C. or lower, 31° C. or lower, 30° C. or lower, 29° C. or lower, 28° C. or lower, 27° C. or lower or 26° C. or lower. However, the temperature is not limited as long as hexanol or butanol can be produced without inhibiting the growth of the microorganism. In an example according to the present disclosure, it was confirmed that the hexanol production amount is increased as the culturing temperature is lower and that hexanol can be produced at high efficiency when the microorganism is cultured at 25-37° C., specifically at 30° C., in consideration of the metabolic rate of the microorganism, etc. (Test Example 1).

The preparation method according to an aspect of the present disclosure may further include a step of stirring the medium to which the synthesis gas has been supplied at a stirring rate of 10-1000 rpm. Specifically, the stirring rate may be 10 rpm or higher, 50 rpm or higher, 60 rpm or higher, 70 rpm or higher, 80 rpm or higher, 90 rpm or higher, 100 rpm or higher, 150 rpm or higher, 200 rpm or higher, 300 rpm or higher, 400 rpm or higher, 600 rpm or higher or 800 rpm or higher, and 1000 rpm or lower, 800 rpm or lower, 600 rpm or lower, 400 rpm or lower, 200 rpm or lower, 180 rpm or lower, 160 rpm or lower, 140 rpm or lower, 120 rpm or lower, 100 rpm or lower, 80 rpm or lower, 60 rpm or lower, 40 rpm or lower or 20 rpm or lower. However, the stirring rate is not limited as long as hexanol or butanol can be produced by supplying synthesis gas repeatedly and the growth of the microorganism is not inhibited.

In the preparation method according to an aspect of the present disclosure, one or more alcohol selected from a group consisting of hexanol and butanol may be prepared by controlling the fermentation condition. The control of the fermentation condition may include addition of ethanol, supply of synthesis gas, control of the supply amount or interval of ethanol or synthesis gas, control of temperature, etc.

Hereinafter, the present disclosure will be described in more detail through examples and test examples. However, the examples and test examples are provided only to be illustrative of the present disclosure and the scope of the present disclosure is not limited by them.

[Test Example 1] Investigation of Synthesis Gas Consumption and Product Production by C. carboxidivorans P7 Depending on Culturing Temperature For preparation of hexanol from synthesis gas through microbial fermentation, fermentation was conducted as described below after supplying synthesis gas. The consumption of synthesis gas and production of hexanol by Clostridium carboxidivorans P7 depending on culturing temperature were investigated at the end of the fermentation.

First, the following media were used. ATCC medium and 1754 PETC medium supplemented with 2 g/L yeast extract, 2 g of ammonium chloride ($NH_4Cl$), g of calcium chloride ($CaCl_2 \cdot 2H_2O$), 0.4 g of magnesium sulfate ($MgSO_4 \cdot 7H_2O$), 0.2 g of potassium chloride (KCl), 0.2 g of potassium phosphate ($KH_2PO_4$), 0.01 g of manganese sulfate ($MnSO_4 \cdot H_2O$), 0.002 g of sodium molybdate ($NaMoO_4 \cdot 2H_2O$), 0.2 g of cysteine and trace elements were used. For pH buffering during the fermentation, 50 mM 2-(N-morpholino)ethanesulfonic acid (MES) was added. The initial pH of the media was adjusted to 6 using 2 M potassium hydroxide (KOH). All the subsequent experiments were carried out using the media.

For batch culture, 20 mL of the medium was added to a 157-mL serum bottle and synthesis gas was supplied at 1.5 bar after inoculating with the microorganism. The synthesis gas consisted of carbon monoxide (CO), carbon dioxide ($CO_2$) and hydrogen ($H_2$) at 30:30:40. The microorganism was cultured in a shaking incubator rotating at a speed of 100 rpm at temperatures of 30° C., 33° C. or 37° C., and the consumption of the gas, the growth of the strain, the change in pH and the product were analyzed with the lapse of time.

The change in the concentration of carbon monoxide (CO), carbon dioxide ($CO_2$) and hydrogen ($H_2$) in the synthesis gas with time was measured using a thermal conductivity detector (TCD) (Agilent Technologies 6890N, USA), and the growth of the strain was monitored by measuring absorbance at 600 nm with a spectrophotometer (Cary 60, Agilent Technologies; CA, USA). The product was analyzed by gas chromatography (Agilent model 6890N gas chromatography).

C. carboxidivorans P7 is one of acetogen strains having the Wood-Ljungdahl pathway. The product produced from the synthesis gas by microbial fermentation of the strain was investigated. As shown in FIGS. 1A-1C, when the synthesis gas ($CO:CO_2:H_2=30:30:40$) was supplied at 1.5 bar, the supplied carbon monoxide was consumed completely and there was no significant difference depending on culturing temperature. However, for hydrogen, the consumption was largest when the culturing was performed at 33° C. The hydrogen consumption was decreased when the culturing temperature was lower (30° C.) or higher (37° C.). In view of hydrogen consumption, it seems that 33° C. is the proper culturing condition. However, the amount of hexanol produced through the fermentation process was inversely proportional to the culturing temperature. That is to say, the hexanol production amount was larger as the culturing temperature was lower (FIG. 1D).

As seen from FIGS. 1A-1D, the hexanol production amount was larger as the culturing temperature was lower. This result is consistent with the research results of Ramió-Pujol et al. (2015) and Shen et al. (2020). But, the production amount of hexanol and butanol was very small (0.1 g/L hexanol and 0.18 g/L at the end of the culturing at 30° C.). It is because the microorganism mainly produces acetic acid to obtain ATP necessary for its growth (FIG. 1E) and produces only small amounts of ethanol, $C_4$ and $C_6$ organic acids and alcohols. But, low culturing temperature is favorable for chain elongation as the metabolism by the microorganism is slowed. Accordingly, the subsequent experiment was by setting the culturing temperature to 25-37° C., specifically to 30° C., for production of hexanol or butanol by C. carboxidivorans P7.

[Test Example 2] Investigation of Carbon Monoxide Consumption and Hexanol and Butanol Production by C. carboxidivorans P7 Depending on Carbon Monoxide Supply Amount According to the result of Test Example 1, very small amount of hexanol and butanol at 0.1 g/L and 0.18 g/L, respectively, was produced when the synthesis gas (CO:$CO_2$:$H_2$=30:30:40) was supplied at 1.5 bar. The major product was acetic acid (FIG. 1E). During the fermentation of synthesis gas, reducing power necessary for production of hexanol is supplied from CO and $H_2$. For improved hexanol production, the CO supply amount needs to be increased. However, the acetogen strain requires adequate supply of CO gas because it is inhibited by CO. In order to identify the CO supply amount that does not inhibit the growth of the strain and the consumption of gas, the amount of hexanol produced by C. carboxidivorans P7 depending on CO supply amount was compared. Experiment was conducted using the same medium as in Test Example 1.

For batch culture, 20 mL of the medium was added to a 157-mL serum bottle and synthesis gas was supplied after inoculating with the microorganism. The synthesis gas consisted of carbon monoxide (CO) and argon (Ar) at 30:70, 50:50 or 70:30 and was supplied at 1.5 bar. The microorganism was cultured in a shaking incubator rotating at a speed of 100 rpm at 30° C., and the consumption of the gas, the growth of the strain, the change in pH and the product were analyzed with the lapse of time.

The change in the concentration of carbon monoxide (CO), carbon dioxide ($CO_2$) and hydrogen ($H_2$) in the synthesis gas with time was measured using a thermal conductivity detector (TCD) (Agilent Technologies 6890N, USA), and the growth of the strain was monitored by measuring absorbance at 600 nm with a spectrophotometer (Cary 60, Agilent Technologies; CA, USA). The product was analyzed by gas chromatography (Agilent model 6890N gas chromatography).

As shown in FIG. 2A, C. carboxidivorans P7 consumed CO gas rapidly without inhibition by CO even when the CO supply amount was increased from 30:70 to 50:50 and to 70:30 as the CO:Ar ratio. As can be seen from FIG. 2B, the hexanol production amount was improved as the amount of consumed CO was increased. Also, the butanol production amount showed a similar tendency to hexanol, increasing from 0.02 g/L to 0.05 g/L and to 0.10 g/L as the proportion of CO in the gas was increased from 30% to 50% and to 70%, respectively. Accordingly, the culturing temperature was set to 30° C., the total gas supply amount to 1.5 bar, and the proportion of CO in the gas to 70%, in order to improve the production of hexanol and butanol.

[Test Example 3] Investigation of Synthesis Gas Consumption and Hexanol and Butanol Production by *C. carboxidivorans* P7 Depending on Additional Supply of Synthesis Gas Based on the results of Test Examples 1 and 2, the production of hexanol was investigated by additionally supplying synthesis gas of the same composition in a fermentation process conducted at 30° C. with a gas supply amount of 1.5 bar and the proportion of CO in the gas at 70%. Experiment was conducted using the same medium as in Test Example 1.

For batch culture, 20 mL of the medium was added to a 157-mL serum bottle and synthesis gas was supplied after inoculating with the microorganism. The synthesis gas consisted of carbon monoxide (CO), carbon dioxide ($CO_2$) and hydrogen ($H_2$) at 70:10:20 and was supplied at 1.5 bar. The microorganism was cultured in a shaking incubator rotating at a speed of 100 rpm at 30° C., and the consumption of the gas, the growth of the strain, the change in pH and the product were analyzed with the lapse of time. Synthesis gas of the same composition was supplied additionally with 72-hour intervals based on the consumption of carbon monoxide (at 0 hour, 72 hours and 144 hours). The microorganism was cultured in a shaking incubator rotating at a speed of 100 rpm at 30° C., and the consumption of the gas, the growth of the strain, the change in pH and the product were analyzed with the lapse of time.

The change in the concentration of carbon monoxide (CO), carbon dioxide ($CO_2$) and hydrogen ($H_2$) in the synthesis gas with time was measured using a thermal conductivity detector (TCD) (Agilent Technologies 6890N, USA), and the growth of the strain was monitored by measuring absorbance at 600 nm with a spectrophotometer (Cary 60, Agilent Technologies; CA, USA). The product was analyzed by gas chromatography (Agilent model 6890N gas chromatography).

As shown in FIG. 3A, *C. carboxidivorans* P7 consumed the supplied CO and $H_2$ gas completely during the fermentation and produced 0.23 g/L hexanol at the end of fermentation (312 hours). *C. carboxidivorans* P7 also consumed the additionally supplied CO gas well (FIG. 3B) and produced 1.22 g/L hexanol (FIG. 3C). Compared to when synthesis gas was not supplied additionally (0.23 g/L), the additional supply resulted in about 5.3 times increased hexanol production (1.22 g/L). Considering that the previously reported maximum hexanol production amount using *C. carboxidivorans* P7 is 0.94 g/L (Phillips et al., 2015), the maximum hexanol production was achieved by optimizing the culturing temperature and the proportion of CO and additionally supplying the synthesis gas. In addition, it was confirmed that the butanol production amount (1.19 g/L) was increased by additionally supplying the synthesis gas as compared to when the synthesis gas was not supplied additionally (0.31 g/L).

[Test Example 4] Investigation of Synthesis Gas Consumption and Hexanol and Butanol Production by *C. carboxidivorans* P7 Depending on Addition of Acetic Acid or Ethanol Based on the results of Test Examples 1-3, experiment was conducted using the same medium composition as in Test Example 1 by adjusting culturing temperature to 30° C. The experiment was conducted while adding acetic acid and ethanol, which are major products of *C. carboxidivorans* P7. The major products of *C. carboxidivorans* P7, acetic acid and ethanol, were added to the medium in order to reduce the production of product. It was intended to improve the production amount of hexanol and butanol by utilizing the carbon source that has been used for the production of acetic acid and ethanol.

[Test Example 4-1] Investigation of Effect of Acetic Acid Addition

For batch culture, 20 mL of the medium was added to a 157-mL serum bottle and synthesis gas was supplied after inoculating with the microorganism. The synthesis gas (CO:$CO_2$:$H_2$=70:10:20) was supplied at 1.5 bar. The production of production was investigated after adding 2.73 g/L sodium acetate (at this time, 2 g/L of acetate was added) in the early stage of fermentation. The microorganism was cultured in a shaking incubator rotating at a speed of 100 rpm at 30° C., and the consumption of the gas, the growth of the strain, the change in pH and the product were analyzed with the lapse of time.

The change in the concentration of carbon monoxide (CO), carbon dioxide ($CO_2$) and hydrogen ($H_2$) in the synthesis gas with time was measured using a thermal conductivity detector (TCD) (Agilent Technologies 6890N, USA), and the growth of the strain was monitored by measuring absorbance at 600 nm with a spectrophotometer (Cary 60, Agilent Technologies; CA, USA). The product was analyzed by gas chromatography (Agilent model 6890N gas chromatography).

As shown in FIGS. 4A and 4B, *C. carboxidivorans* P7 produced mainly acetic acid during the fermentation while consuming the supplied CO and $H_2$ gas. At the end of the fermentation (216 hours), the products were mainly organic acids as 1.30 g/L acetic acid, 0.66 g/L butyric acid and 0.80 g/L hexanoic acid. The production amount of hexanol and butanol was merely 0.25 g/L and 0.21 g/L, respectively.

The presence of acetic acid in the medium leads to decreased production of acetic acid, and the carbon source that has been used for the production of acetic acid is utilized for the production of hexanol and butanol. Therefore, in order to improve the productivity of hexanol and butanol, fermentation was conducted by adding acetic acid, which is the major product of *C. carboxidivorans* P7, at the early stage of the fermentation. The result is shown in FIGS. 4C and 4D. When acetic acid was added, the consumption of CO gas was facilitated at the early stage of the fermentation (48 hours), and the consumption of hydrogen was increased (FIG. 4C) as compared to when acetic acid was not added (FIG. 4A). However, the addition of acetic acid did not affect the production of hexanol and butanol. At the end of the fermentation (216 hours), 1.14 g/L acetic acid, 1.20 g/L butyric acid and 0.79 g/L hexanoic acid were produced. But, the production of hexanol (0.11 g/L) was decreased by 2.27 times owing to the addition of acetic acid. In addition, the production of butanol (0.18 g/L) was decreased due to the addition of acetic acid. That is to say, the addition of acetic acid increased the production of butyric acid but decreased the production of hexanol and butanol.

The acetogens converts synthesis gas to acetyl-CoA using the Wood-Ljungdahl pathway and produces acetic acid from the acetyl-CoA in order to obtain ATP necessary for its growth. That is to say, *C. carboxidivorans* P7 produced acetic acid to obtain ATP necessary for its growth regardless of the addition of acetic acid.

[Test Example 4-2] Investigation of Effect of Ethanol Addition

It was intended to investigate the effect of the addition of ethanol, which is known as the major product of the acetogen strain, to the medium on fermentation. It was intended to reduce ethanol production by adding ethanol and, thereby, utilize the carbon source for hexanol and butanol production instead of production of ethanol. It was also investigated whether the productivity of hexanol and butanol can be improved by focusing the limited reducing power obtained from synthesis gas on the production of hexanol and butanol instead of ethanol.

Specifically, experiment was conducted in the same manner as in Test Example 4-1 except for adding 2 g/L ethanol instead of sodium acetate at the early stage of fermentation and the production of hexanol and butanol was investigated. As a result, the addition of ethanol during the early stage of fermentation had no significant effect on the consumption of the supplied synthesis gas (FIG. 4E). At the end of the fermentation, the production of organic acids was similar to Test Example 4-1 (FIG. 4B) as 1.38 g/L acetic acid, 0.69 g/L butyric acid and 0.78 g/L hexanoic acid (FIG. 4F). Meanwhile, the production of butanol and hexanol was increased significantly as the initially added ethanol was decreased. For butanol, the production amount was 0.21 g/L and 0.18 g/L for a non-added test group and an acetic acid-added test group, respectively, but the production amount was increased to 0.69 g/L by about 3-4 times when ethanol was added. In addition, for hexanol, whereas the production amount was 0.25 g/L (FIG. 4B) and 0.11 g/L (FIG. 4d) for the non-added test group and the acetic acid-added test group, respectively, the production amount was increased to 0.76 g/L when ethanol was added (FIG. 4F). This corresponds to increase by 3.04 times as compared to the non-added test group (FIG. 4B) and 6.91 times as compared to the acetic acid-added test group (FIG. 4D). It is though that the productivity of the $C_4$ and $C_6$ alcohols was increased as the reducing power was utilized for chain elongation owing to the addition of ethanol.

In Test Examples 4-1 and 4-2, it was intended to reduce the production of $C_2$ products by adding acetic acid and ethanol, which are major products of C. carboxidivorans P7, and utilize the carbon source effectively for the production of $C_4$ and $C_6$ products. However, the production amount of acetic acid was not decreased because the microorganism produced acetic acid to obtain ATP necessary for its growth. It was intended to reduce ethanol production by adding ethanol to the medium and, thereby, utilize the carbon source for hexanol and butanol production instead of production of ethanol. The production of hexanol and butanol was increased unexpectedly as C. carboxidivorans P7 consumed the added ethanol. It is thought that the reducing power that had been obtained by consuming ethanol was used for the production of hexanol and butanol. Therefore, the economic efficiency of production of valuable $C_4$ and $C_6$ alcohols can be improved by using the inexpensive ethanol.

[Test Example 5] Investigation of Synthesis Gas Consumption and Product Production by C. carboxidivorans P7 During Additional Supply of Synthesis Gas Depending on Whether Ethanol is Added In Test Example 3, the additional supply of synthesis gas improved hexanol production. In addition, in Test Example 4, it was confirmed that the addition of ethanol to the medium decreases ethanol and increases the production of hexanol and butanol. Therefore, the effect of addition of ethanol during the additional supply of synthesis gas on the production of hexanol and butanol was investigated.

For batch culture, 20 mL of the medium was added to a 157-mL serum bottle and synthesis gas was supplied after inoculating with the microorganism. The synthesis gas consisted of carbon monoxide (CO) and argon (Ar) at 70:30 and was supplied at 1.5 bar. Synthesis gas of the same composition was supplied additionally with 72-hour intervals based on the consumption of carbon monoxide (at hour, 72 hours and 144 hours). The microorganism was cultured in a shaking incubator rotating at a speed of 100 rpm at 30° C., and the consumption of the gas, the growth of the strain, the change in pH and the product were analyzed with the lapse of time.

The change in the concentration of carbon monoxide (CO), carbon dioxide ($CO_2$) and hydrogen ($H_2$) in the synthesis gas with time was measured using a thermal conductivity detector (TCD) (Agilent Technologies 6890N, USA), and the growth of the strain was monitored by measuring absorbance at 600 nm with a spectrophotometer (Cary 60, Agilent Technologies; CA, USA). The product was analyzed by gas chromatography (Agilent model 6890N gas chromatography).

As shown in FIGS. 5A and 5B, the additionally supplied CO was consumed regardless of the addition of ethanol. Also, as shown in FIG. 5C, the test group to which only the synthesis gas was supplied additionally without the addition of ethanol mainly produced acetic acid during the early stage of fermentation, but the alcohol production was increased as the produced acetic acid was decreased. When the synthesis gas was supplied additionally during the fermentation, the major products were alcohols as 1.21 g/L ethanol, 1.21 g/L butanol and 1.90 g/L hexanol (FIG. 5C). Whereas the major products were organic acids when the fermentation was conducted without additional supply of the synthesis gas as shown in FIG. 4B, the additional supply of the synthesis gas resulted in improved alcohol productivity owing to the reducing power supplied from carbon monoxide. The hexanol and butanol production amount was the maximum amount achieved using the synthesis gas.

In addition, as shown in FIG. 5D, when ethanol was added to the medium and the synthesis gas was supplied additionally during the fermentation process, the added ethanol was decreased rapidly and, at the same time, the $C_6$ alcohol was produced rapidly from the early stage of fermentation (FIGS. 5C and 5D). Whereas the production of ethanol was increased when ethanol was not added (FIG. 5C), the production of ethanol was decreased and production of ethanol hexanol and butanol was increased when ethanol was added. At the end of fermentation (312 hours), butanol and hexanol were produced at 1.60 g/L and 2.34 g/L, respectively. The production amount of the alcohols was increased as the reducing power derived from the synthesis gas and ethanol was used.

In summary, by additionally supplying synthesis gas to a medium inoculated with a strain producing one or more alcohol selected from a group consisting of hexanol and butanol, hexanol or butanol can be prepared without genetic manipulation of the microorganism, catalysis, etc. In particular, the productivity of hexanol or butanol can be improved by adjusting the residual amount of carbon monoxide in the synthesis gas, reaction temperature and the supply amount of the synthesis gas. In addition, when ethanol is added to the medium besides the additional supply of the synthesis gas, the productivity of hexanol or butanol is improved as the ethanol is consumed.

Statement Regarding Prior Disclosures by the Inventor or a Joint Inventor

The inventors of the present application have made related disclosure in Hyun Ju O H et al., "Effect of Culture Conditions on Hexanol Production from Syngas by *Clostridium carboxidivorans* P7," 2021 KSBB Spring Meeting and International Symposium, Apr. 14-16, 2021. The related disclosure was made less than one year before the effective filing date (Sep. 17, 2021) of the present application and the inventors of the present application are the same as those of the related disclosure. Accordingly, the related disclosure is disqualified as prior art under 35 USC 102(a)(1) against the present application. See 35 USC 102(b)(1)(A).

The invention claimed is:

1. A culture medium composition for preparing an alcohol, wherein
    the alcohol is one or more alcohol selected from a group consisting of hexanol and butanol,
    the composition comprises ethanol as an active ingredient in an amount of 0.2-20 g/L based on the total volume of a medium in which the medium composition is comprised,
    the alcohol is prepared from synthesis gas, and
    the composition is for culturing a strain producing the alcohol.

2. The culture medium composition for preparing an alcohol according to claim 1, wherein the strain producing the alcohol is one or more selected from a group consisting of *Clostridium carboxidivorans* and *Clostridium ragsdalei*.

3. The culture medium composition for preparing an alcohol according to claim 1, wherein the synthesis gas comprises carbon monoxide.

4. The culture medium composition for preparing an alcohol according to claim 3, wherein the synthesis gas further comprises one or more selected from a group consisting of carbon dioxide and hydrogen.

5. The culture medium composition for preparing an alcohol according to claim 1, wherein the synthesis gas is an additionally supplied synthesis gas.

6. The culture medium composition for preparing an alcohol according to claim 1, wherein the alcohol is prepared at 25-37° C.

7. The culture medium composition for preparing an alcohol according to claim 1, wherein the composition comprises ethanol as an active ingredient in an amount of 1.1-20 g/L based on the total volume of a medium in which the medium composition is comprised.

* * * * *